US011266853B2

(12) United States Patent
Kothari et al.

(10) Patent No.: US 11,266,853 B2
(45) Date of Patent: Mar. 8, 2022

(54) INTRAORAL PHOTOTHERAPY DEVICES

(71) Applicant: Lumitex Inc., Strongsville, OH (US)

(72) Inventors: Vedang Kothari, Strongsville, OH (US); Peter Broer, Strongsville, OH (US)

(*) Notice: Subject to any disclaimer, the term of this patent is extended or adjusted under 35 U.S.C. 154(b) by 471 days.

(21) Appl. No.: 15/758,586

(22) PCT Filed: Sep. 12, 2016

(86) PCT No.: PCT/US2016/051259
§ 371 (c)(1),
(2) Date: Mar. 8, 2018

(87) PCT Pub. No.: WO2017/044931
PCT Pub. Date: Mar. 16, 2017

(65) Prior Publication Data
US 2018/0304092 A1 Oct. 25, 2018

Related U.S. Application Data

(60) Provisional application No. 62/216,825, filed on Sep. 10, 2015.

(51) Int. Cl.
*A61N 5/06* (2006.01)
*A61B 17/00* (2006.01)
(Continued)

(52) U.S. Cl.
CPC .......... *A61N 5/0603* (2013.01); *A61N 5/0624* (2013.01); *A61B 2017/00035* (2013.01);
(Continued)

(58) Field of Classification Search
CPC ...... A61N 5/0603; A61N 5/0624; A61N 5/06; A61N 5/0601; A61N 2005/005;
(Continued)

(56) References Cited

U.S. PATENT DOCUMENTS

| 4,852,549 A | 8/1989 | Mori |
| 5,297,960 A * | 3/1994 | Burns .................. A61C 9/0006 433/41 |

(Continued)

FOREIGN PATENT DOCUMENTS

| DE | 20 2011 104169 U1 | 10/2011 |
| GB | 2 475 623 A | 5/2011 |

(Continued)

OTHER PUBLICATIONS

International Search Report and Written Opinion for corresponding Patent Application No. PCT/US2016/051259 dated Mar. 1, 2017.

(Continued)

*Primary Examiner* — Yogesh P Patel
(74) *Attorney, Agent, or Firm* — Wickens Herzer Panza

(57) ABSTRACT

Intraoral phototherapy devices receive light from an associated light source and propagate the light into an oral cavity of a patient. The device comprises a light guide that receives light from an external light source. The light guide comprises a main body portion made of an optically transparent soft flexible biocompatible polymeric material sized and shaped to conform to contours of the oral cavity when inserted therein to direct the light to targeted regions of the oral cavity. The main body portion comprises a pair of spaced apart side wings sized and shaped to be received between a patient's teeth and cheeks on opposite sides of the oral cavity and a center flap intermediate the side wings for transmitting and directing the light to targeted regions of the oral cavity. A controller delivers light to the light guide in a controlled manner.

13 Claims, 19 Drawing Sheets

(51) Int. Cl.
*A61B 18/00* (2006.01)
*A61N 5/00* (2006.01)
*A61B 90/00* (2016.01)

(52) U.S. Cl.
CPC ............... *A61B 2017/00084* (2013.01); *A61B 2018/00791* (2013.01); *A61B 2018/00839* (2013.01); *A61B 2090/034* (2016.02); *A61N 2005/005* (2013.01); *A61N 2005/063* (2013.01); *A61N 2005/0606* (2013.01); *A61N 2005/0626* (2013.01); *A61N 2005/0645* (2013.01); *A61N 2005/0651* (2013.01); *A61N 2005/0666* (2013.01)

(58) Field of Classification Search
CPC .... A61N 2005/0606; A61N 2005/0603; A61N 2005/0626; A61N 2005/0645; A61N 2005/0651; A61N 2005/0666; A61C 19/066; A61C 2008/0046; A61C 2008/0084
USPC ..................................................... 433/29, 215
See application file for complete search history.

(56) References Cited

U.S. PATENT DOCUMENTS

| | | | | |
|---|---|---|---|---|
| 5,487,662 | A * | 1/1996 | Kipke | A61C 9/0006 433/215 |
| 2005/0221251 | A1 * | 10/2005 | Soukos | A61N 5/0601 433/29 |
| 2006/0019214 | A1 * | 1/2006 | Lawrence | A61C 19/063 433/29 |
| 2006/0141422 | A1 * | 6/2006 | K. Philp | A61C 19/066 433/215 |
| 2008/0032252 | A1 * | 2/2008 | Hayman | A61B 5/0088 433/29 |
| 2008/0294227 | A1 | 11/2008 | Perez | |
| 2010/0151407 | A1 | 6/2010 | Rizoiu et al. | |
| 2011/0104633 | A1 * | 5/2011 | Levine | A61C 19/063 433/29 |
| 2012/0214122 | A1 * | 8/2012 | Dwyer | A61C 19/066 433/29 |
| 2015/0132709 | A1 * | 5/2015 | Park | A61C 19/066 433/29 |

FOREIGN PATENT DOCUMENTS

| | | |
|---|---|---|
| GB | 2 475 623 B | 10/2012 |
| WO | 98/06456 A1 | 2/1998 |
| WO | 2008/124918 A1 | 10/2008 |

OTHER PUBLICATIONS

Second Written Opinion for corresponding Patent Application No. PCT/US2016/051259 dated Aug. 24, 2017.
International Preliminary Report on Patentability for corresponding Patent Application No. PCT/US2016/051259 dated Jan. 4, 2018.

* cited by examiner

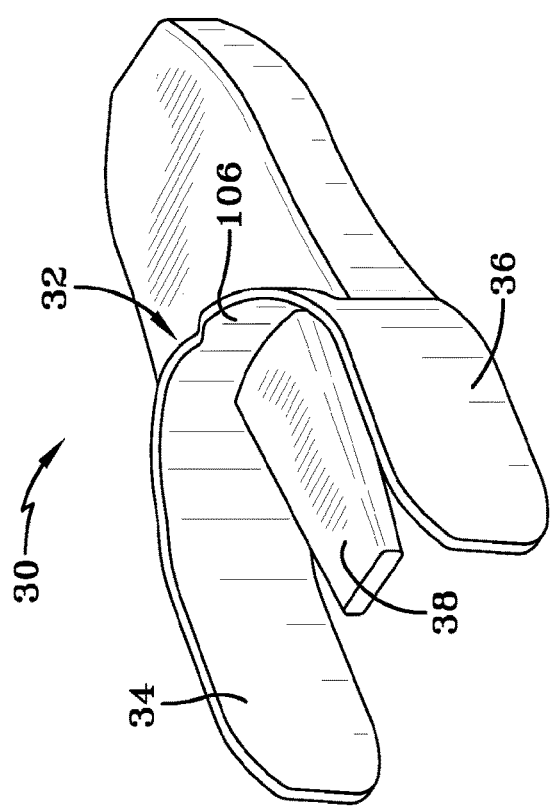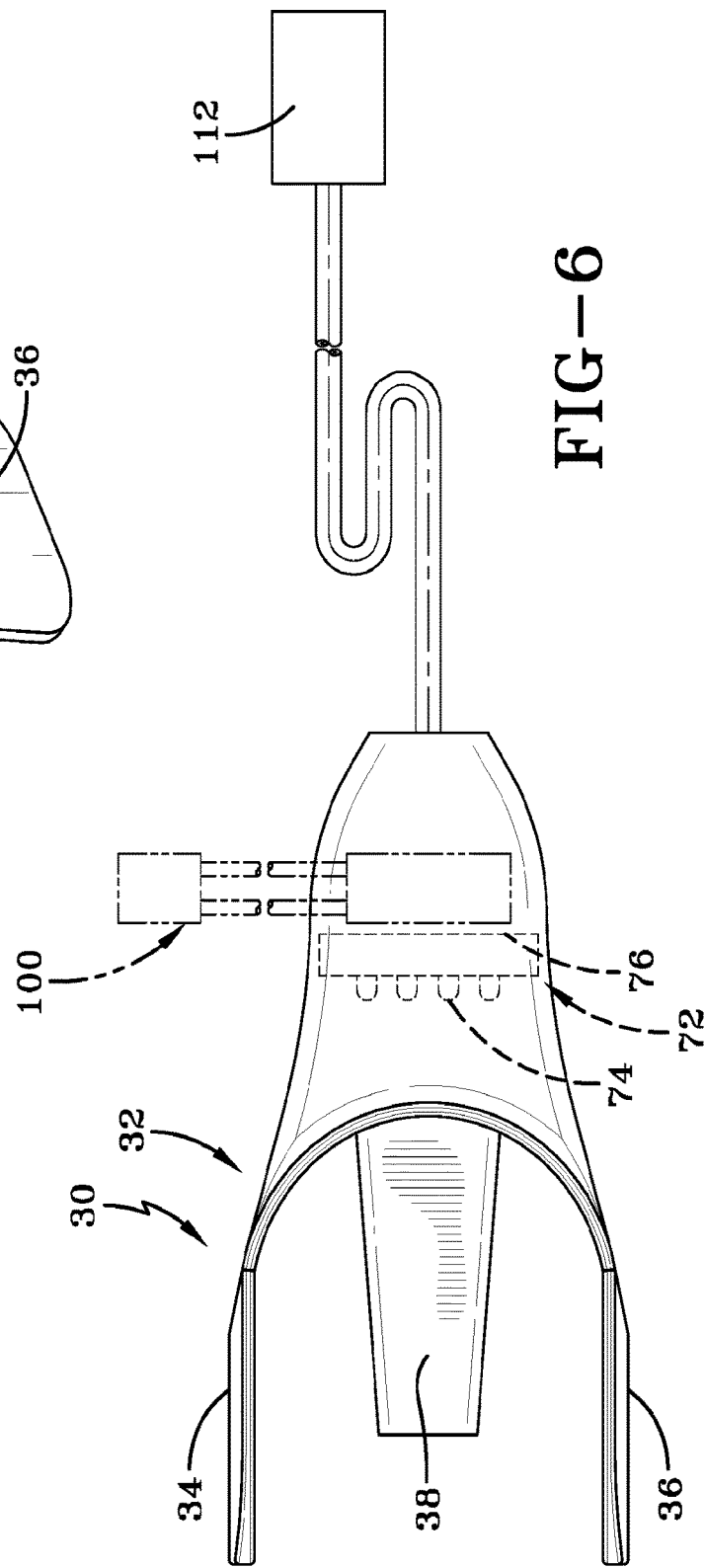

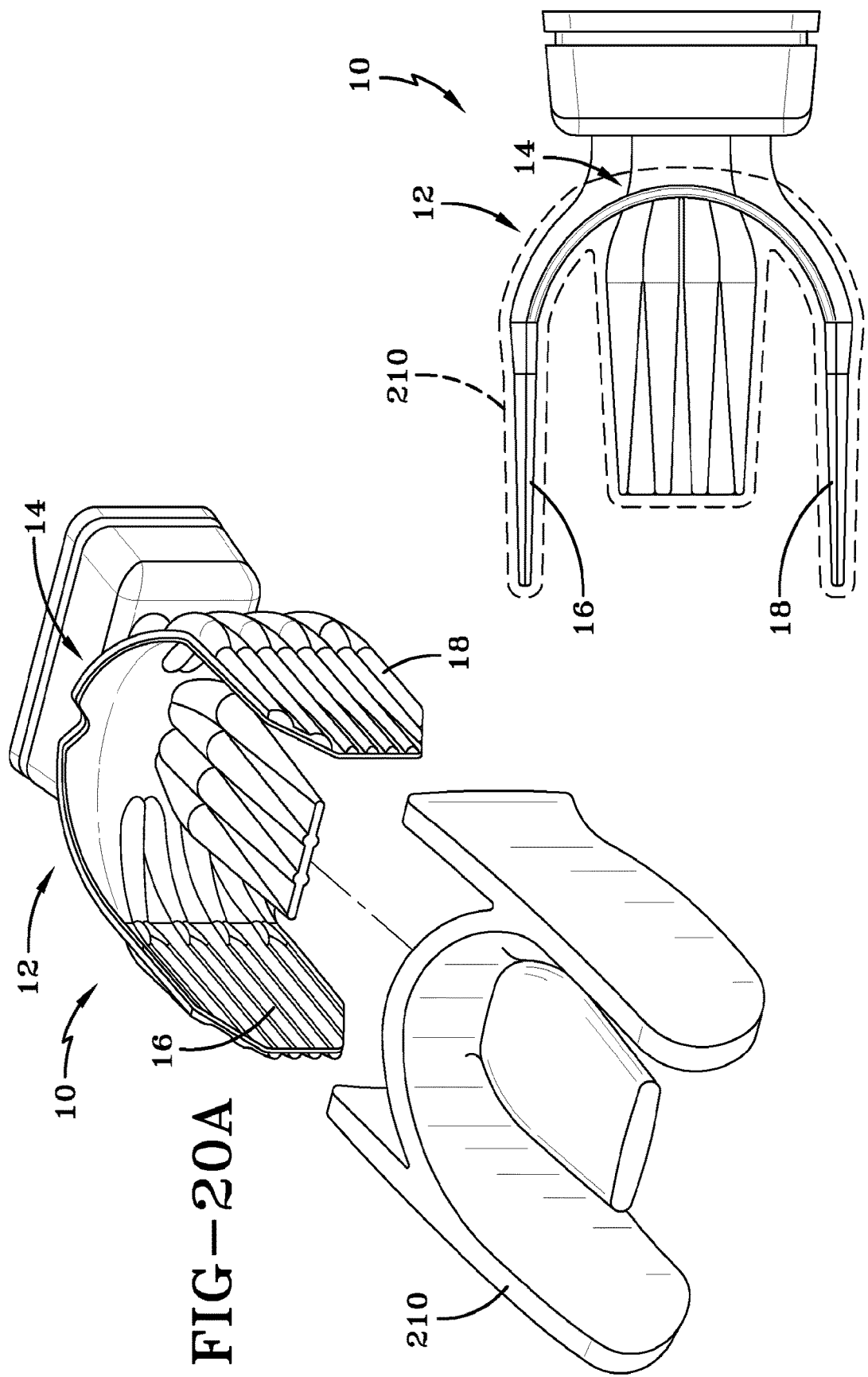

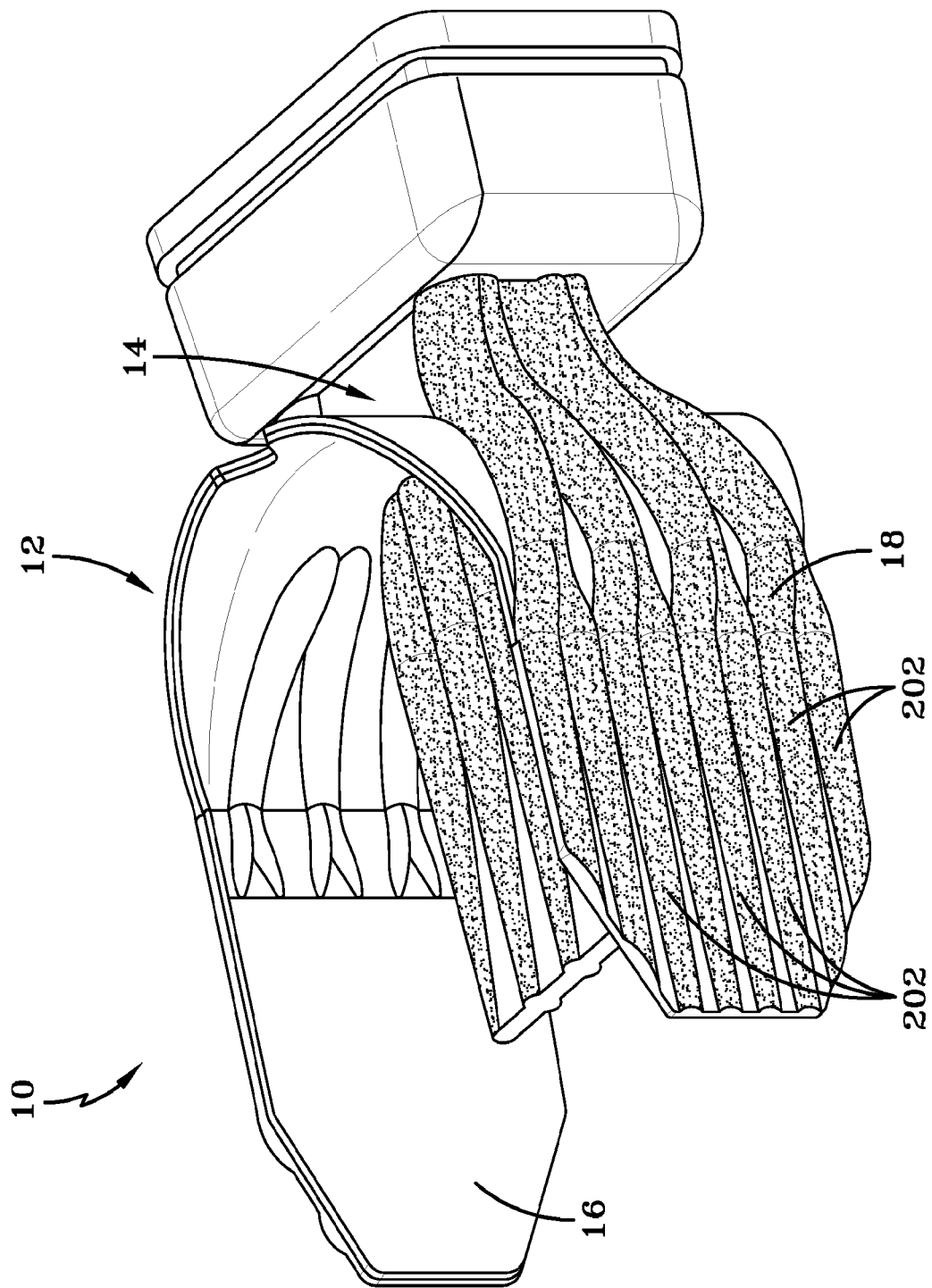

INTRAORAL PHOTOTHERAPY DEVICES

RELATED APPLICATIONS

This application claims priority to International Application No. PCT/US2016/051259 filed Sep. 12, 2016, which claims the benefit of U.S. 62/216,825 filed Sep. 10, 2015. Which are both herein incorporated by reference in their entirety.

TECHNICAL FIELD

This invention relates generally to intraoral phototherapy devices for receiving light from an associated light source and propagating the light into the oral cavity of a patient by total internal reflection and emission for phototherapy treatment of targeted regions of the oral cavity.

BACKGROUND

Currently there are two known methods for administering phototherapy for the treatment of various phototherapy treatment conditions of the mouth including, but not limited to Oral Mucositis (OM), low level laser therapy and light emitting diode (LED) arrays. Oral Mucositis is one of the most common and highly significant toxicities of cancer therapy.

Barriers to the acceptance of low level laser therapy include the cost of laser equipment and the labor intensiveness. Additionally, there are problems with interoperator variability and the need for specialized training. Also patients receiving this form of treatment are required to hold their mouths open for long periods of time which is uncomfortable and becomes extremely painful as the Mucositis progresses.

LED arrays utilize a plurality of LEDs to irradiate larger areas of tissue externally. The light from these arrays penetrates the skin to stimulate the mucosal membrane. LED arrays have the advantage of irradiating a large surface area, are simpler to implement than spot laser systems, and are more comfortable to the patient. The main disadvantages of using LED arrays for administering phototherapy treatment is that they lack dose control because they must transilluminate cheek tissue and have difficulty reaching all regions of the oral cavity, including the tonsillar and palatal regions which are highly susceptible to OM. Also variability in tissue thickness between different buccal regions and different patients makes it impossible to accurately monitor and control the dose of light administered to the mucosa.

SUMMARY

The present invention relates to intraoral phototherapy devices that can achieve greater accuracy of phototherapy dose control compared to the use of LED arrays and spot laser therapy by directly delivering light to targeted regions of the oral cavity.

In an embodiment, the intraoral phototherapy device comprises a light guide that receives light from an external light source, the light guide comprising a main body portion made of an optically transparent soft flexible biocompatible polymeric material sized and shaped to conform to contours of the oral cavity to direct the light to targeted regions of the oral cavity.

In an embodiment, the main body portion comprises a pair of laterally spaced side wings sized and shaped to be received between a patient's teeth and cheeks on opposite sides of the oral cavity for transmitting and directing the light to targeted regions of the oral cavity.

In an embodiment, the side wings support one or more solid side light channels integrally molded with the side wings, the side light channels being generally cylindrical in shape and selectively tapered along their length for controlled light emission therefrom.

In an embodiment, the side light channels utilize splitting to more evenly distribute the light to targeted regions of the oral cavity.

In an embodiment, the main body portion further comprises a center flap that can go on top of the patient's tongue for tonsillar projection and hard and soft palate phototherapy treatment or under the tongue.

In an embodiment, one or more light sources are optically coupled to rearwardly protruding end portions of the device.

In an embodiment, the light source comprises one or more LEDs that are embedded in rearwardly protruding end portions of the side light channels and center flap.

In an embodiment, the light source is remotely coupled to the device via a fiber optic cable.

In an embodiment, the remote light source comprises a plurality of LEDs or a laser.

In an embodiment, the device further comprises integral top and bottom flaps that fit between a patient's gums and lips to help stabilize the device against rotation in the oral cavity during phototherapy treatment.

In an embodiment, the device further comprises bite pads for securing the side wings in the oral cavity during phototherapy treatment.

BRIEF DESCRIPTION OF THE DRAWINGS

FIG. 5 is a front perspective view of an embodiment of an intraoral phototherapy device.

FIG. 6 is a top plane view of the phototherapy device of FIG. 5.

FIGS. 20A-20B show a phototherapy device and a sleeve.

FIG. 26 shows a phototherapy device including a roughened surface.

DETAILED DESCRIPTION

Figure 1:
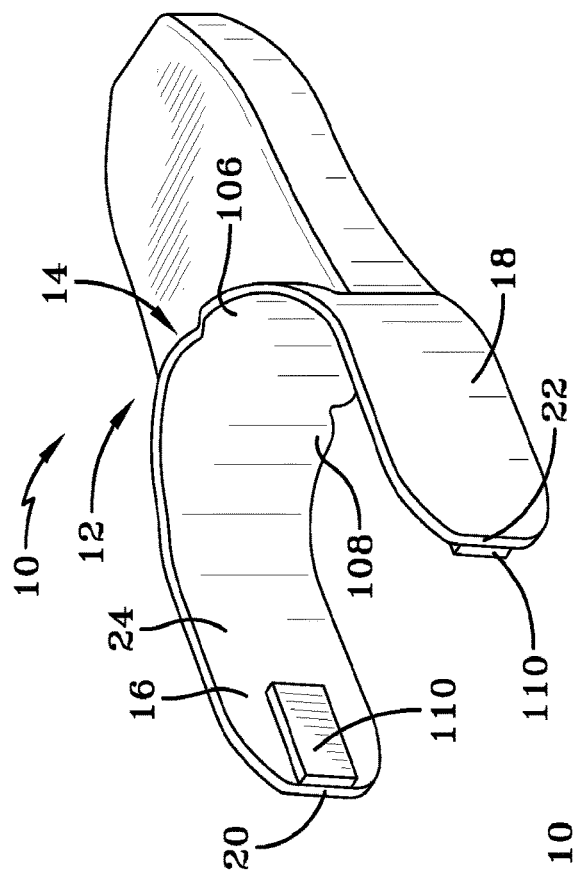
FIG. 1 is a front perspective view of an embodiment of an intraoral phototherapy device.

Referring now more particularly to the drawings, wherein the same reference numbers are used to designate like parts, and initially to FIGS. 1-4, there is shown an embodiment of an intraoral phototherapy device 10 comprising a light guide 12 that receives light from an external light source. In all of the embodiments disclosed herein, the light guide 12 comprises a main body portion 14 made of an optically transparent soft flexible biocompatible polymeric material such as silicone. However, the body portion 14 may be made of other optically clear biocompatible soft polymeric materials as well including but not limited to different formulations of polycarbonate, polymethyl methacrylate, polystyrene, nylon, acrylonitrile butadiene styrene, polyolefin, or other biocompatible thermoplastic elastomer formulations.

The intraoral phototherapy device may be used in a number of applications, several examples of which include oral mucositis, acute necrotizing ulcerative gingivitis (ANUG), periodontal diseases, trismus, decreasing recovery time from oral surgery, light delivery for orthodontics, and photodynamic light therapy, e.g., to activate a chemical mouthwash.

In the embodiment shown in FIGS. 1-4, the main body portion 14 comprises a pair of laterally spaced side wings 16, 18 sized and shaped to be received between a patient's teeth and cheeks on opposite sides of the oral cavity for transmitting and directing light to targeted regions of the oral cavity by internal reflection and causing light to be emitted therefrom by providing disruptions or lenses 23 along the length of the side wings. Also the innermost ends 20, 22 of the side wings may project light to other targeted regions of the oral cavity.

In any of the embodiments, a reflective coating 24 may be provided on the inwardly facing sides of the side wings to reflect light out through the outwardly facing sides of the side wings.

In any of the embodiments, the side wings may have a curvature that is contoured to mandibular and maxillary buccal surfaces of the oral cavity for emitting light thereto.

FIGS. 5 and 6 show an embodiment of an intraoral phototherapy device 30 in which the main body portion 32 includes, in addition to side wings 34, 36, a center flap 38 intermediate the side wings for transmitting and directing light to other targeted regions of the oral cavity. The center flap 38 can go on top of the patient's tongue for tonsillar projection and hard and soft palate phototherapy treatment or under the tongue.

FIGS. 9-14 show an embodiment of an intraoral phototherapy device 40 in which the main body portion 42 includes one or more side light channels 44, 46 integrally molded with the side wings 48, 50 for transmitting and directing light to targeted regions of the oral cavity. In an embodiment, the side light channels 44, 46 are generally solid and cylindrical in shape and are selectively tapered along their length for controlled light emission therefrom.

In an embodiment, each of the side light channels 44, 46 utilizes splitting to more evenly distribute the light to the targeted regions of the oral cavity. For example, each of the side light channels 44, 46 may have two or more branches 52, 54 to more evenly distribute the light to the targeted regions of the oral cavity. Also each of the branches 52, 54 may have two or more additional branches 56, 58 to further more evenly distribute the light to the targeted regions of the oral cavity.

In an embodiment, each of the side light channels and/or branches is selectively tapered and/or has disruptions or lenses along their length for controlled light emission therefrom. Also in any of the embodiments, a reflective coating 24 may be applied to the inwardly facing sides of the side wings to reflect light outwardly through the outwardly facing sides of the side wings/side light channels including the side light channel branches.

In the embodiment shown in FIGS. 9-14, the center flap 60 intermediate the side wings 48, 50 includes one or more center light channels 62, 64 that may be selectively tapered on at least one side for controlled light emission therefrom. Also the center light channels 62, 64 may have two or more branches 66, 68 to more evenly distribute the light to targeted regions of the oral cavity. Further, one of the sides of the center light channels 62, 64 may have a flat reflective portion (see FIG. 10) for reflecting light out the other side of the center light channels.

In an embodiment, at least one of the sides of the center light channels 62, 64 may have disruptions or lens patterns along their length to cause light to be emitted therefrom in a controlled manner.

Figure 7:
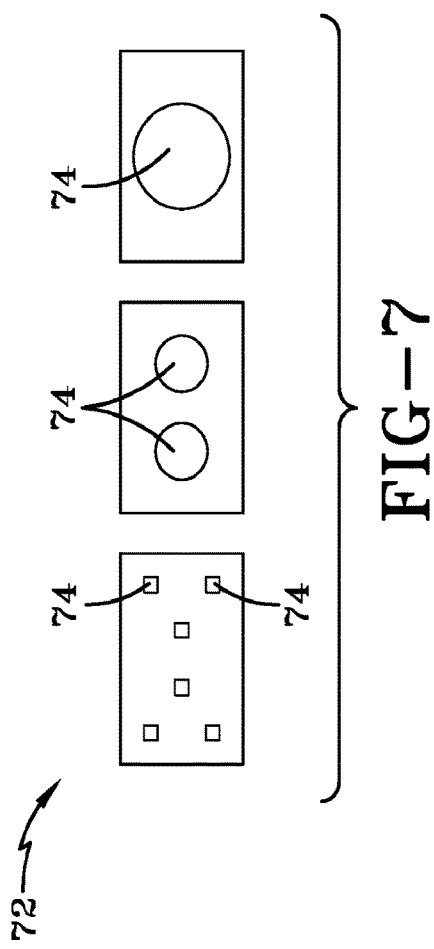
FIG. 7 is a schematic illustration of different LED light source configurations for various embodiments of the intraoral phototherapy device.
Figure 10:
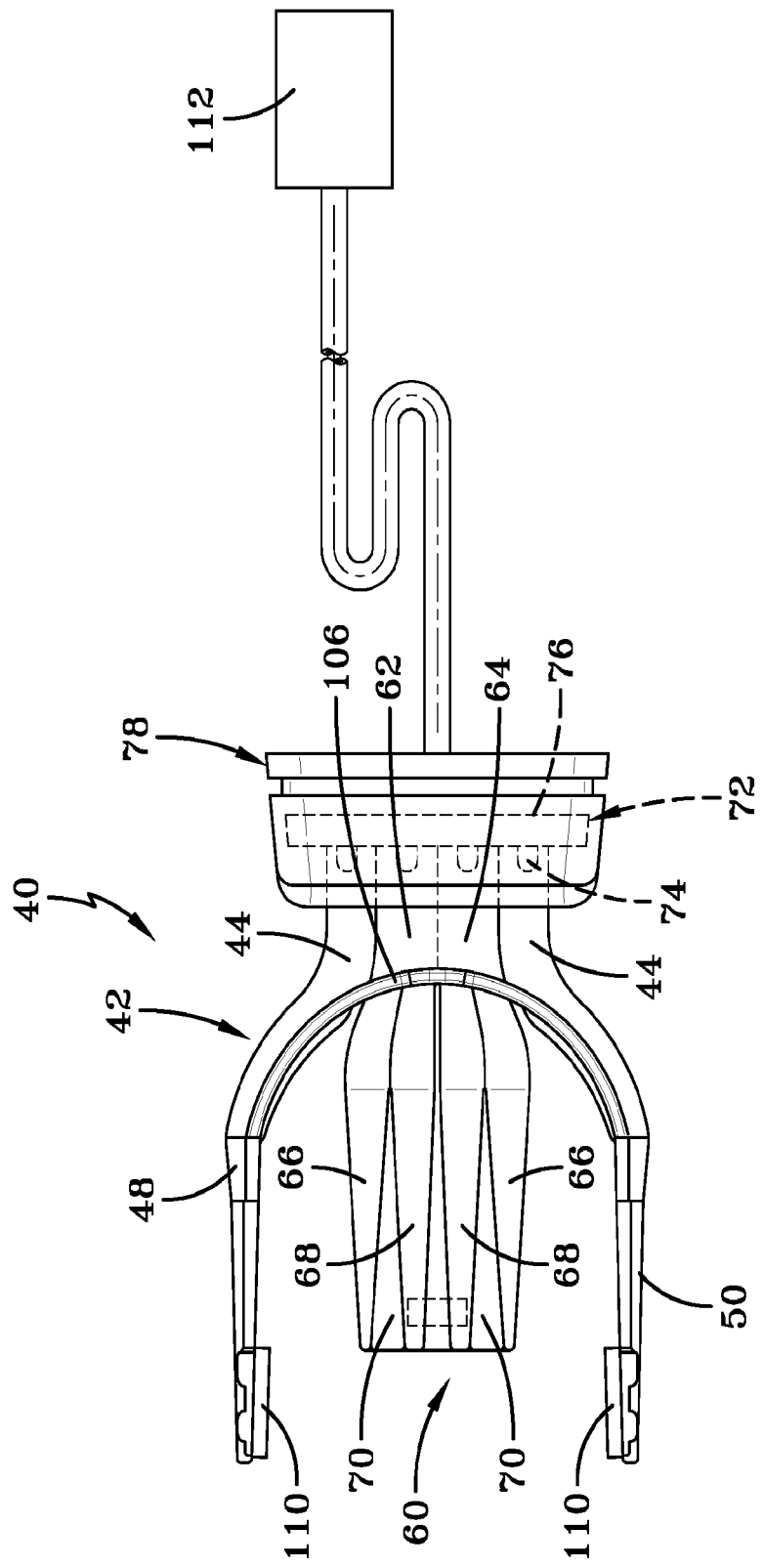
FIG. 10 is a top plane view of the phototherapy device of FIG. 9.
Figure 11:
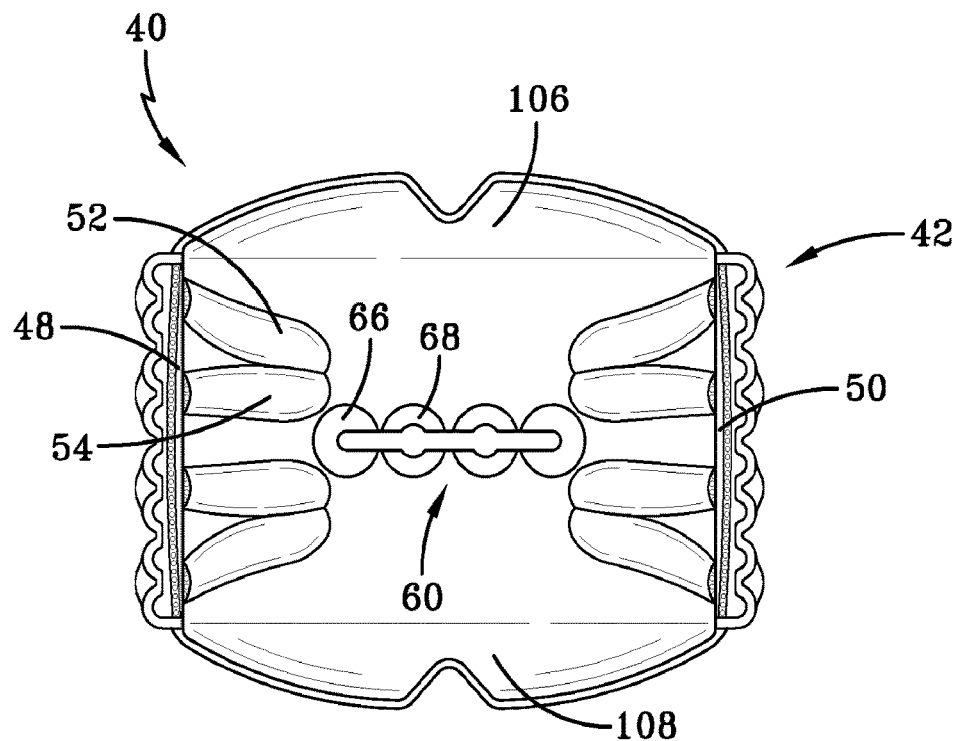
FIG. 11 is a front view of the phototherapy device of FIG. 9.
Figure 12:
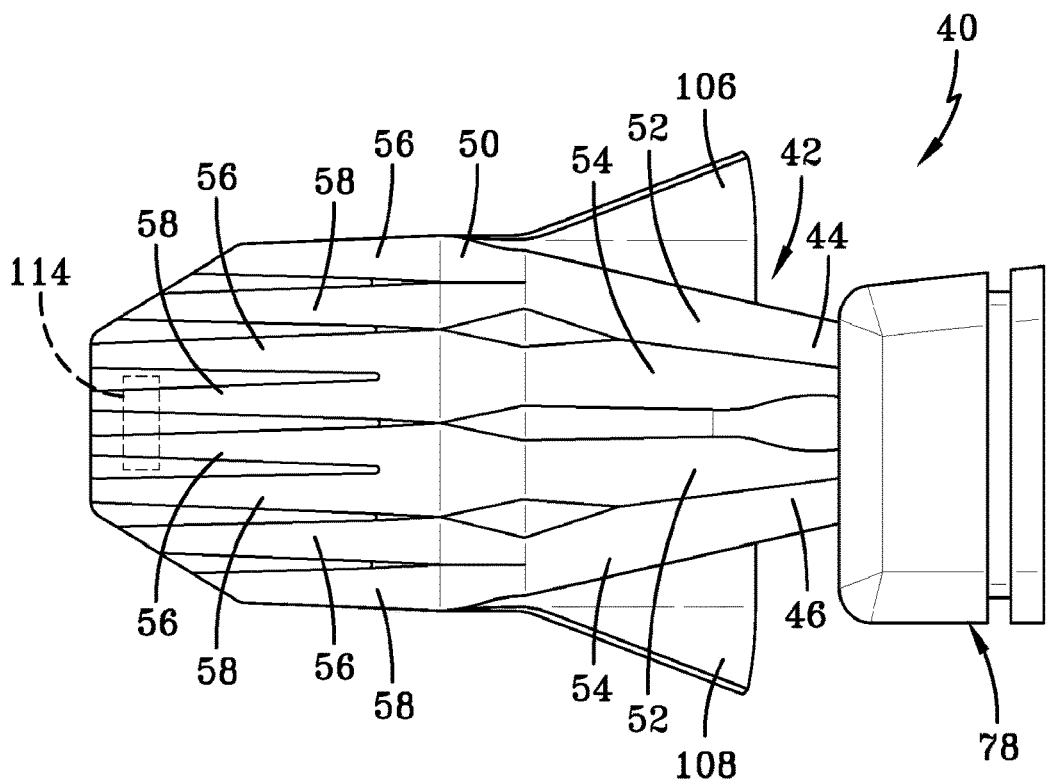
FIG. 12 is a side view of the phototherapy device of FIG. 9.
Figure 13:
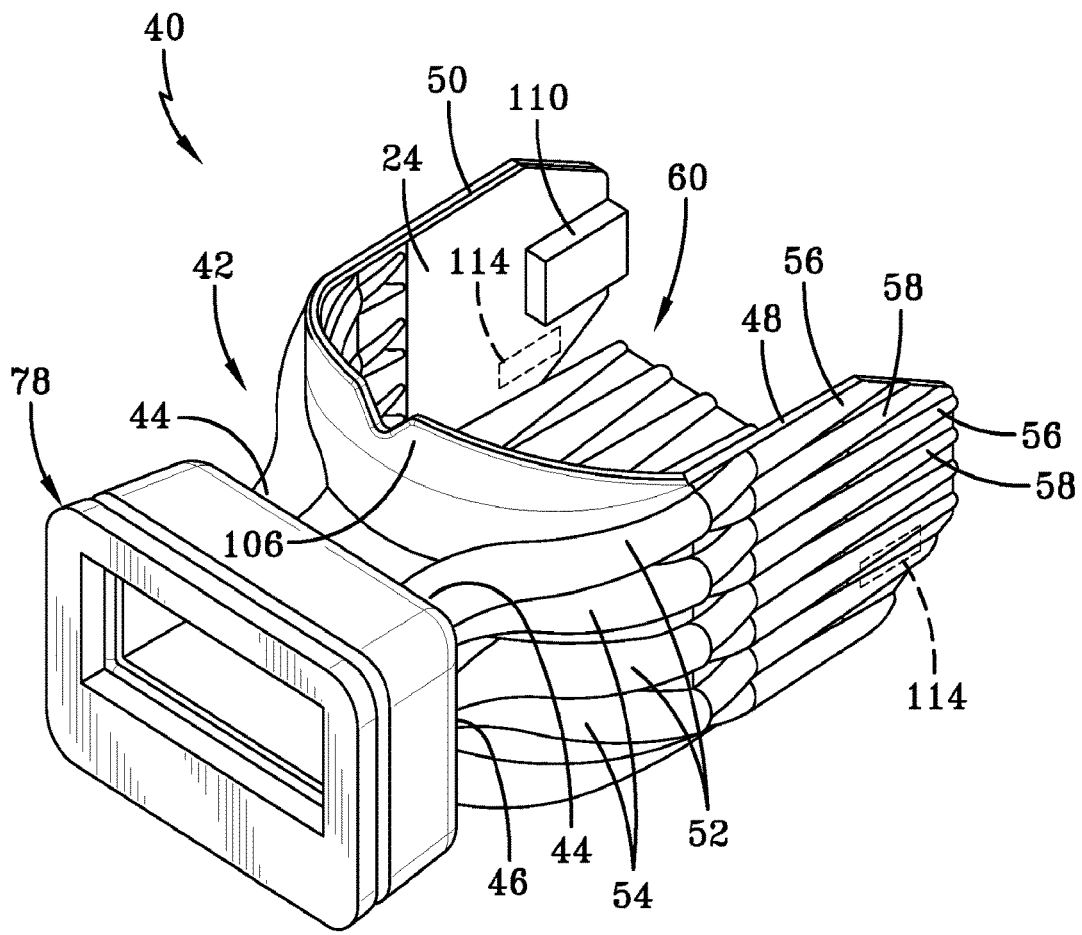
FIG. 13 is a rear perspective view of the intraoral device of FIG. 9.
Figure 14:
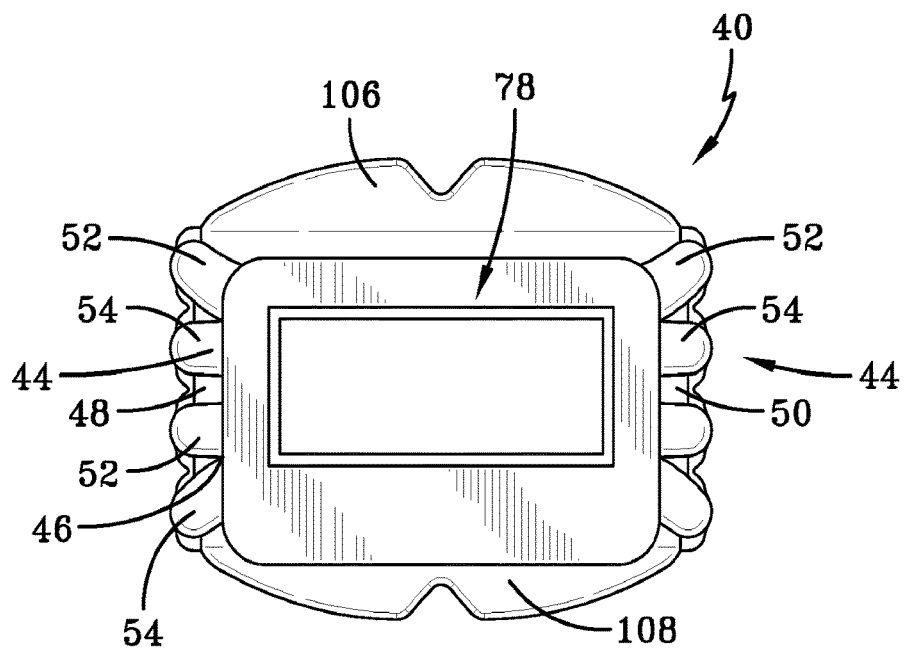
FIG. 14 is a rear view of the intraoral device of FIG. 9.

In all of the embodiments, one or more portions of the main body portion protrude rearwardly beyond the side wings for optically coupling of a light source 72 thereto. In the embodiments shown in FIGS. 1-4, 5-6 and 9-14, respectively, the light source 72 comprises one or more LEDs 74 directly optically coupled to rearwardly protruding ends of the main body portion. The light source 72 may comprise multiple light sources 72 and the output of the light sources 72 may vary in optical power. FIG. 7 shows several different exemplary LED configurations including as few as one relatively high powered LED 74 or two or more lesser powered LEDs 74 that may be mounted on a circuit board 76 inside a housing 78 attached to the rearwardly protruding ends of the main body portion with the LEDs 74 in substantially direct contact with the protruding ends or embedded therein as schematically shown in FIG. 10.

Figure 8:
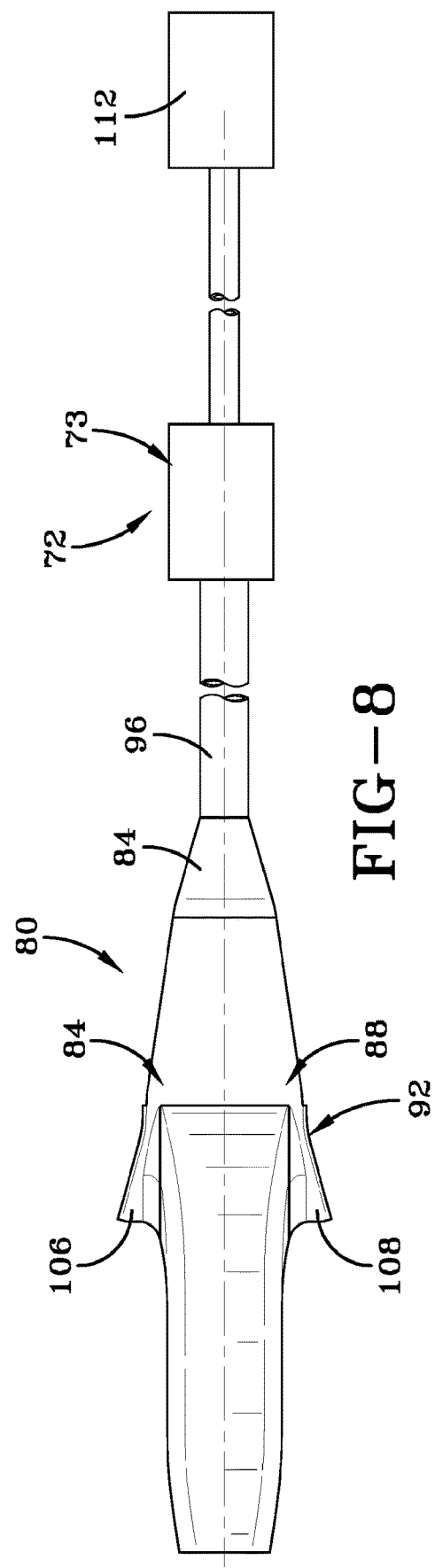
FIG. 8 is a side view of an embodiment of an intraoral phototherapy device.
Figure 9:
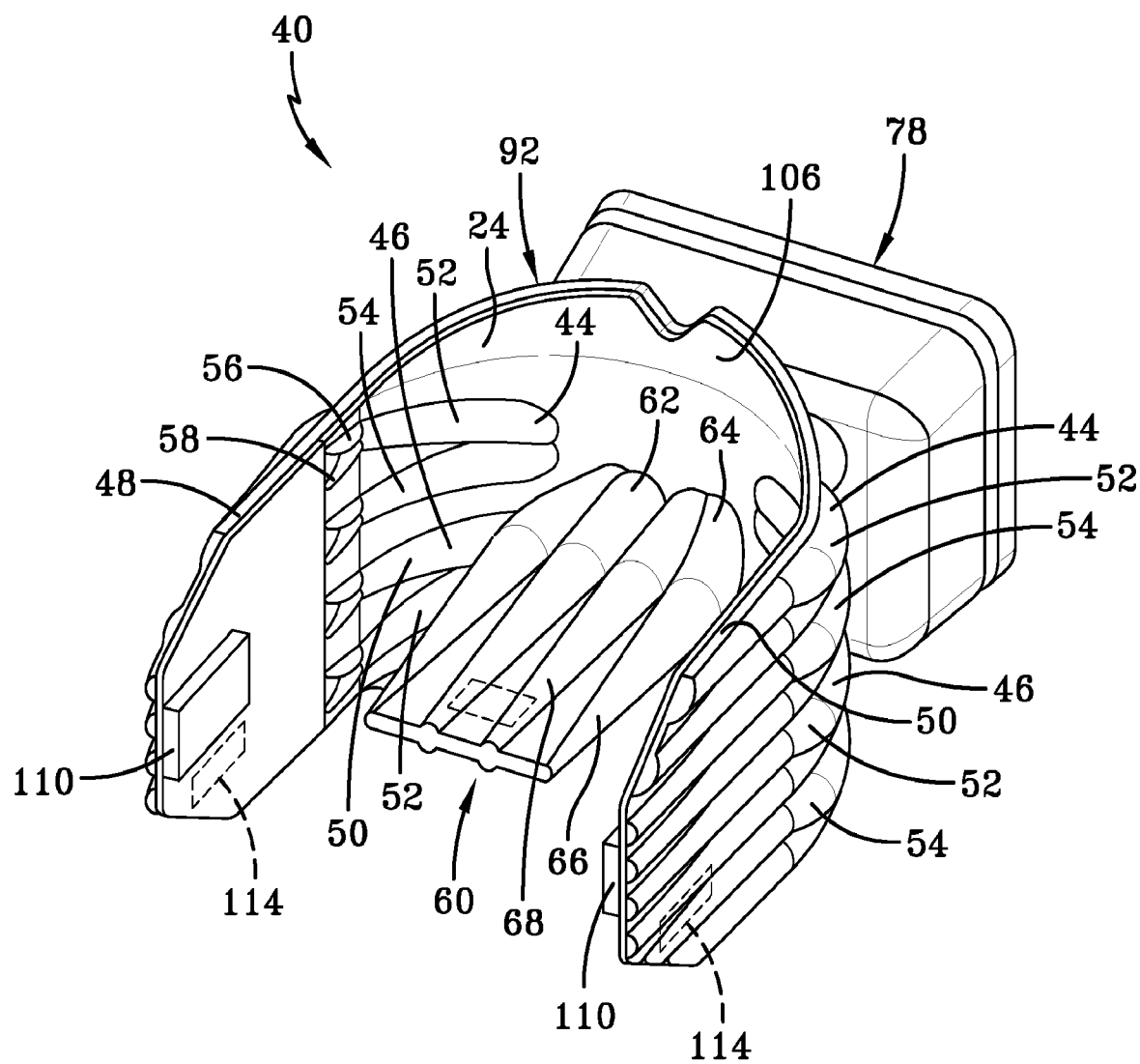
FIG. 9 is a front perspective view of an embodiment of an intraoral phototherapy device.
Figure 15:
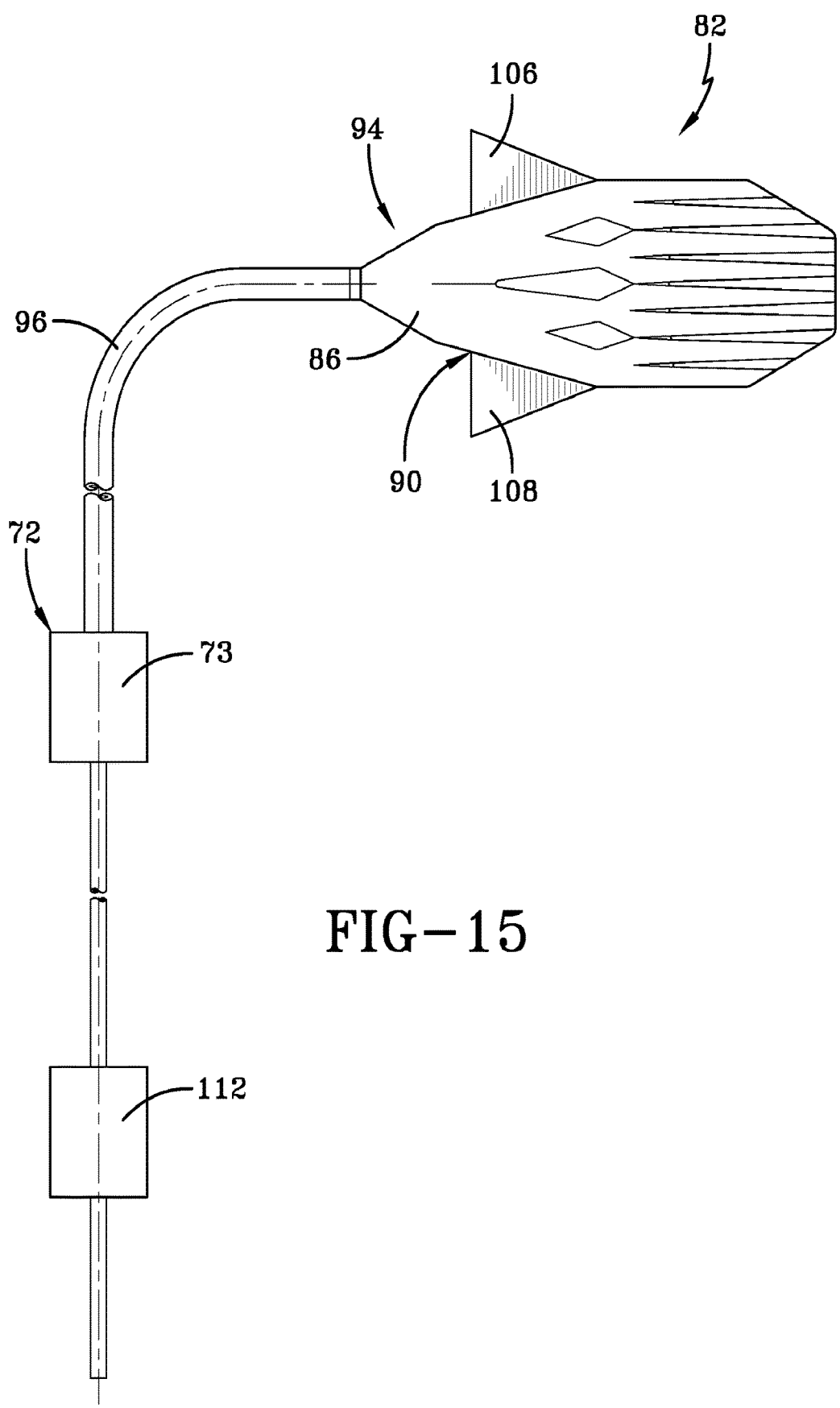
FIG. 15 is a side view of an embodiment of an intraoral phototherapy device.

In other intraoral phototherapy embodiments 80 and 82 shown in FIGS. 8 and 15, respectively, the light source 72 is a remote light source 73 that is optically coupled to rearwardly protruding ends 84, 86 of the respective main body portions 88, 90 of the light guides 92, 94 via a fiber optic cable 96.

In an embodiment, the remote light source 73 comprises one or more LEDs or a laser.

Figure 2:
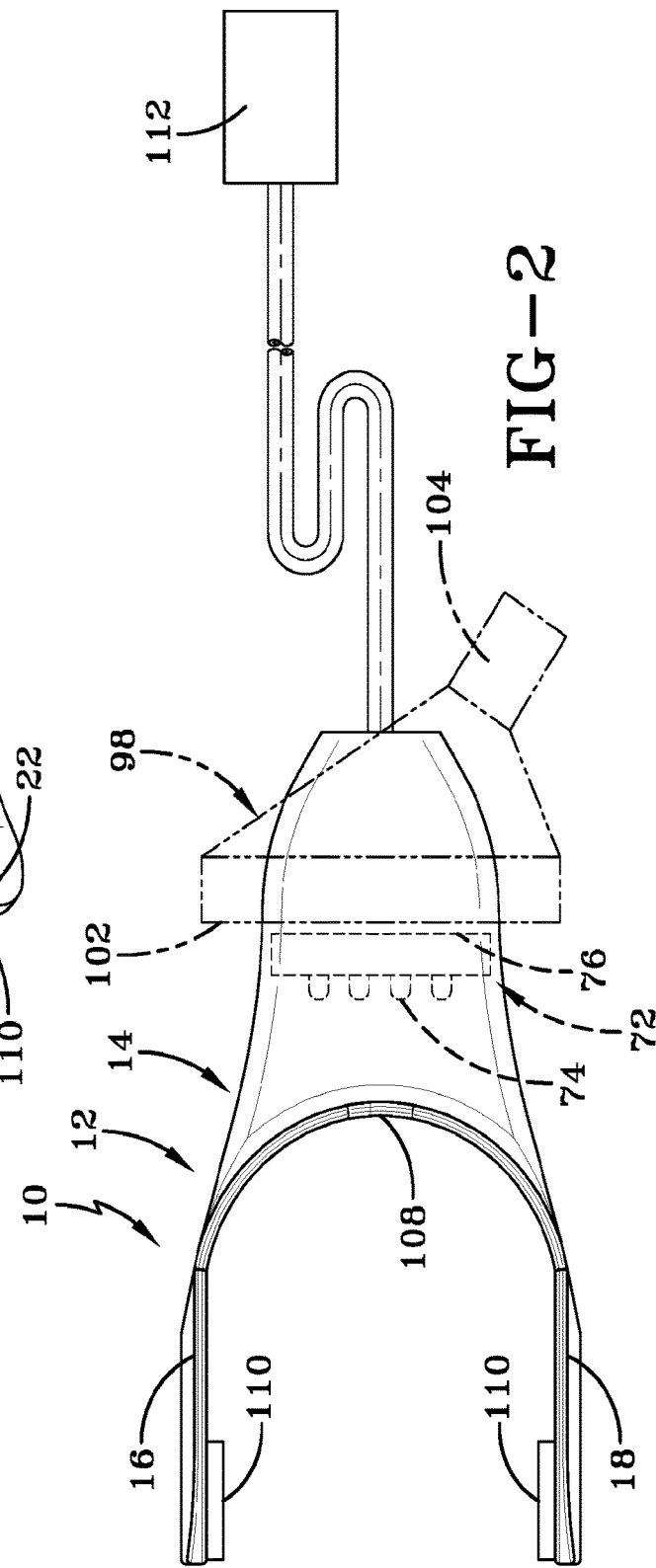
FIG. 2 is a top plane view of the phototherapy device of FIG. 1.
Figure 3:
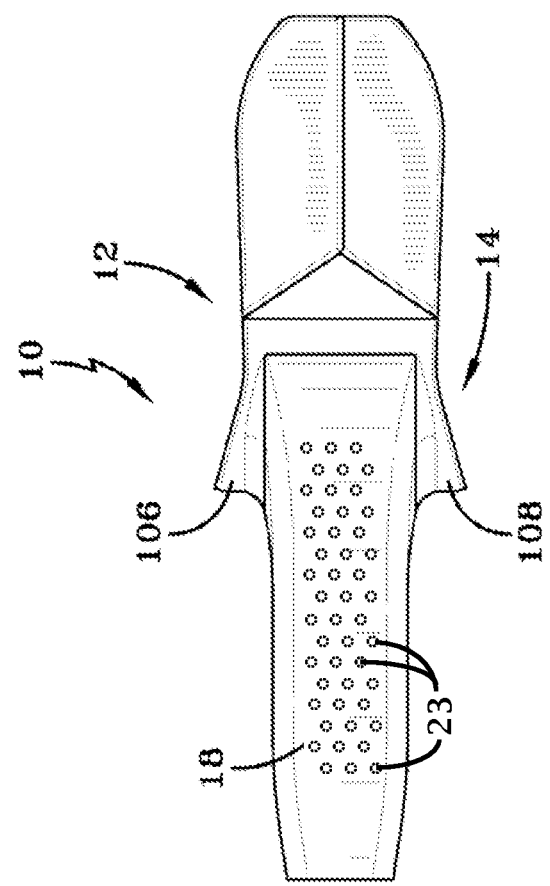
FIG. 3 is a side view of the phototherapy device of FIG. 1.
Figure 4:
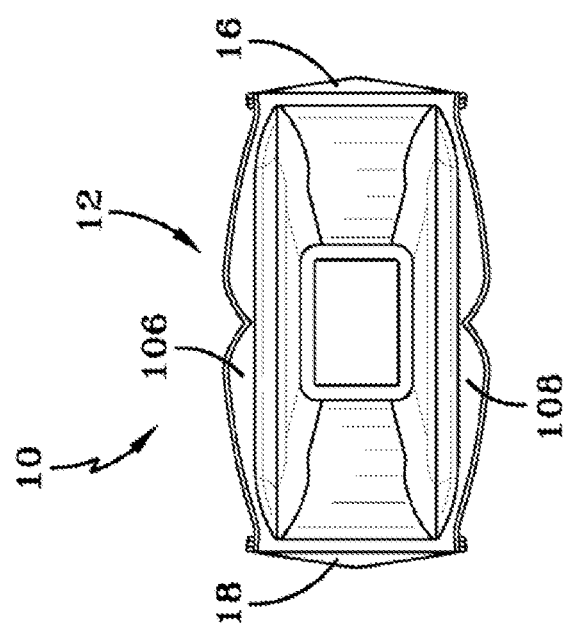
FIG. 4 is a rear view of the phototherapy device of FIG. 1.

In an embodiment, a cooling system 98, 100 is provided for extracting heat away from the light source 72 (see FIGS. 2 and 6).

In the embodiment shown in FIG. 2, the cooling system 98 comprises a heat sink 102 which may include a fan 104 for moving air past the heat sink to aid in the cooling process.

In the embodiment shown in FIG. 6, the cooling system 100 comprises a liquid cooling system. For example, in FIG. 13 a liquid cooling chamber 77 is shown.

In any of the embodiments, the intraoral phototherapy devices may include integral arcuate flexible top and bottom flaps 106, 108 that protrude upwardly and downwardly from the arcuate joined rearward ends of the side wings for insertion between a patient's gums and lips to help stabilize the devices against rotation during phototherapy treatment.

In any of the embodiments, the intraoral phototherapy devices may include bite pads 110 on the inwardly facing sides of the side wings intermediate the height thereof adjacent the innermost ends of the side wings as shown for example in FIGS. 1, 2, 9, 10 and 13 for engagement by the patient's molar teeth to secure the side wings in place during phototherapy treatment.

In any of the embodiments, the intraoral phototherapy device comprises a controller 112 (see FIGS. 2, 6, 8, 10, 15 and 16) for delivering light to the light guide in a controlled manner.

In any of the embodiments, the controller 112 may deliver constant light, pulsating light and/or multiple wavelengths of light to the light guide.

In any of the embodiments, the controller may include one or more sensors 114 (see FIGS. 9, 12, 13) that monitor one or more of temperature, pH, salinity, moisture, humidity, conductivity and resistivity in the oral cavity during phototherapy treatment.

In any of the embodiments, the controller 112 may transmit data wirelessly from the oral cavity during phototherapy treatment.

In any of the embodiments, the controller 112 may monitor light output from the light source and change input power to the light source to self-calibrate the light output from the light source.

Figure 16:
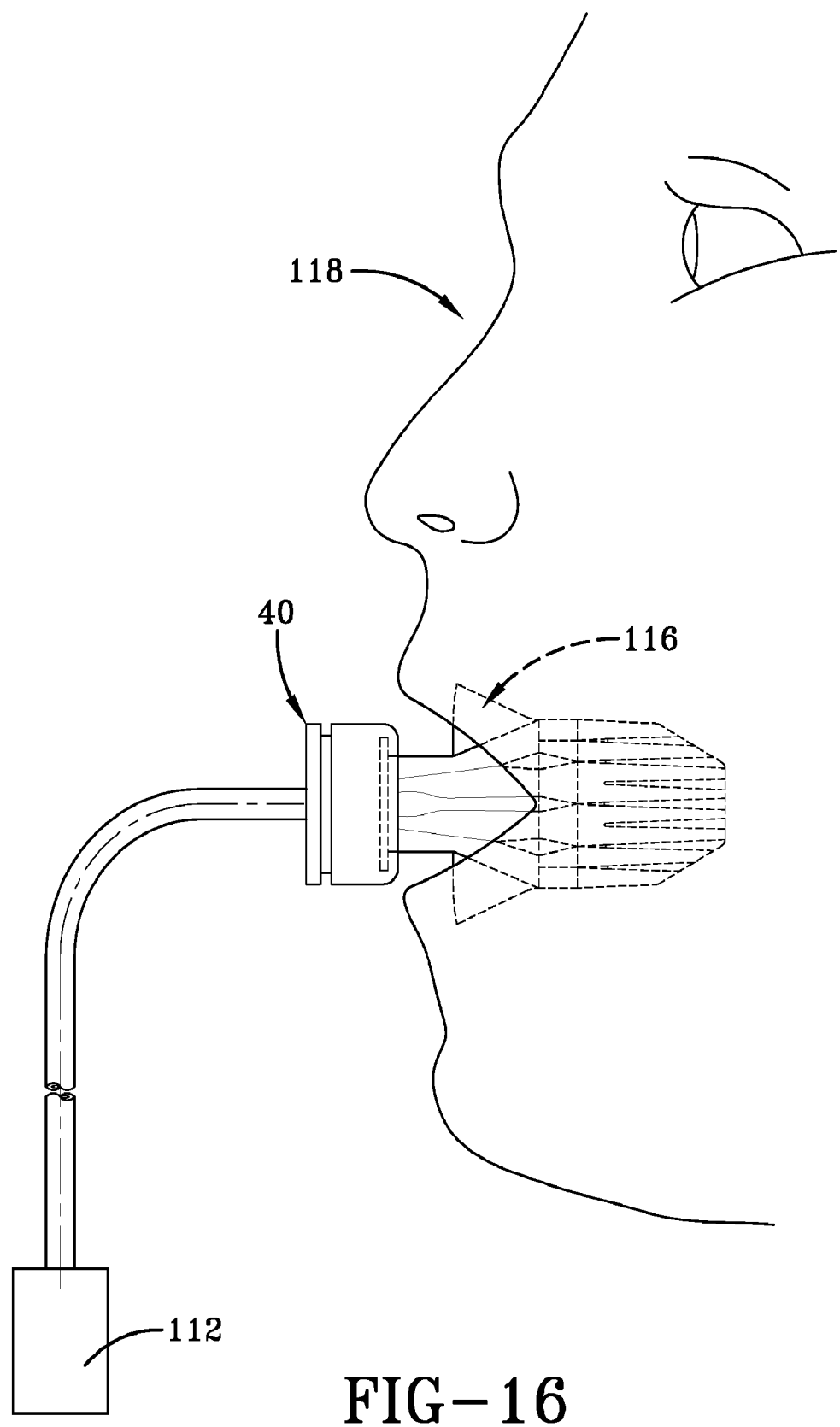
FIG. 16 is a schematic side view of an embodiment of an intraoral phototherapy device inserted into the oral cavity of a patient with the mouth substantially closed.
Figure 17:
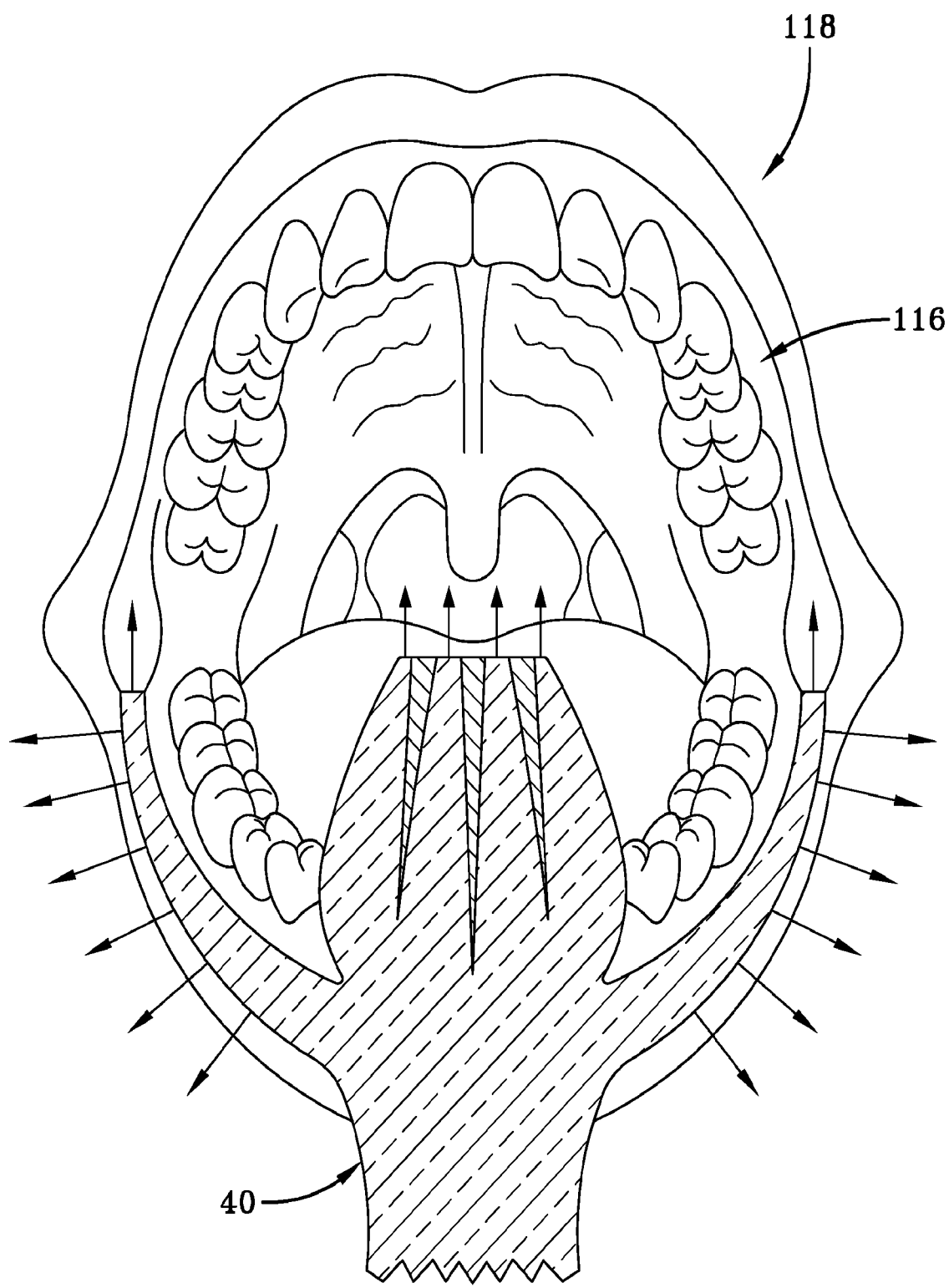
FIG. 17 is a schematic longitudinal section through the phototherapy device of FIG. 16 as viewed from the front with the patient's mouth wide open.
Figure 18A:
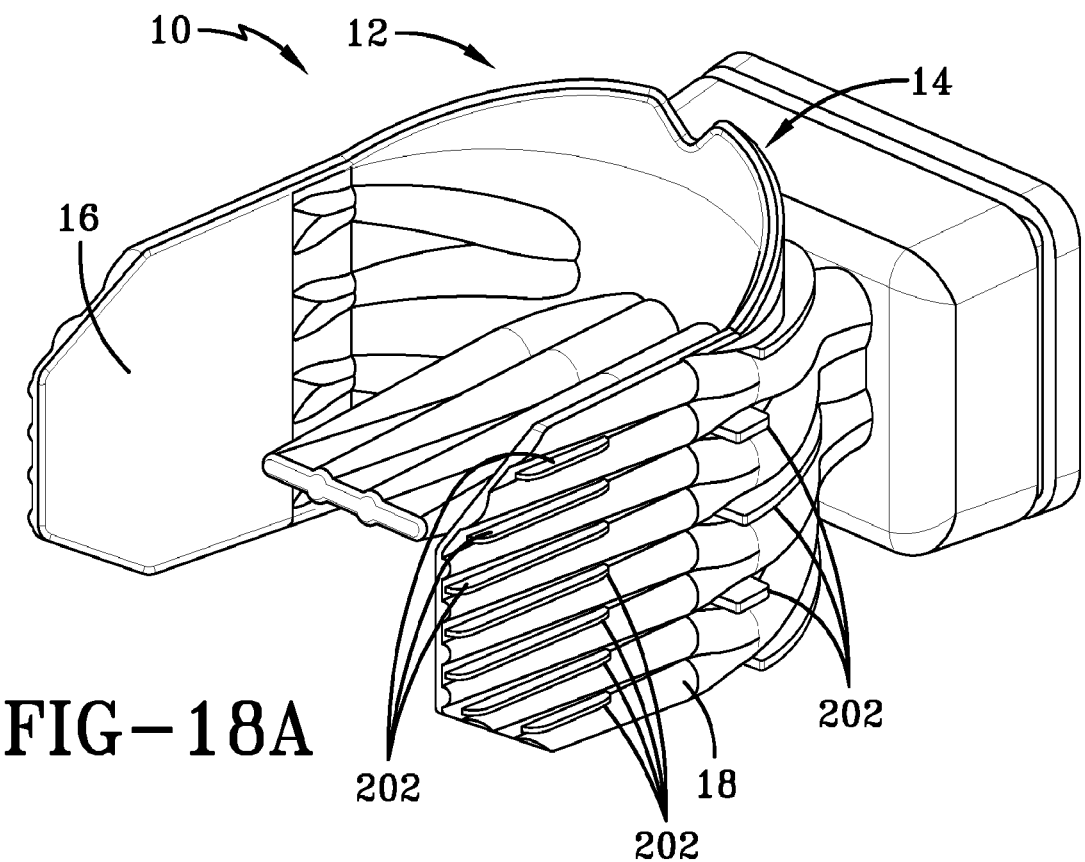
FIGS. 18A-18C and 19A-19C show a phototherapy device including separating features.
Figure 18B:
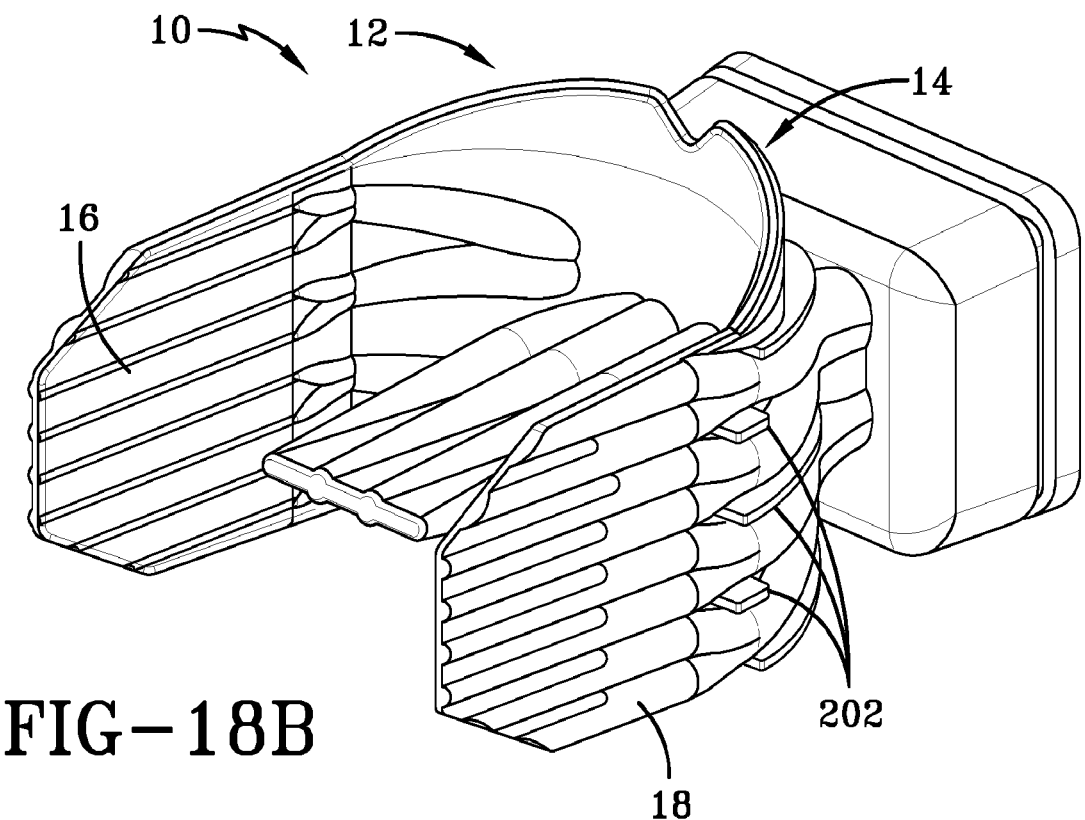

FIGS. 16 and 17 schematically show how the intraoral phototherapy device 40 of FIGS. 9-14 fits within the oral cavity 116 of a patient 118 and emits or directs light therefrom to targeted regions of the oral cavity.

To maintain uniform light delivery to the patient, an air gap may be provided around the intraoral phototherapy device. When the intraoral phototherapy device is placed in the mouth, the air gap around the intraoral phototherapy device may be inconsistent depending on the volume and location of saliva in the mouth and the location of contact with tissue. When an air gap is present, the lower index of refraction of air results in light being maintained in the intraoral phototherapy device due to total internal reflection (TIR). However, the index of refraction of saliva and tissue is higher than air and, for this reason, at the points of contact between the intraoral phototherapy device and saliva or tissue may result in light being emitted from the intraoral phototherapy device at the points of contact. The variability in the contact between the intraoral phototherapy device and saliva and tissue (both between patients and between sessions for a single patient) may make uniform light delivery a challenge. For this reason, an air gap may be maintained between the intraoral phototherapy device and tissue and saliva in order to maintain TIR.

As shown in FIGS. 20A-20B, to maintain an airgap around the intraoral phototherapy device, a sleeve 210 (e.g., a disposable plastic sleeve) or cover may be utilized around the intraoral phototherapy device. For example, FIG. 20B shows that the sleeve 210 (represented by dotted lines) may be of a shape to receive the main body portion 14 of the intraoral phototherapy device. The sleeve 210 may be made of a very thin, flexible, optically transparent and medical grade material. The sleeve may also act as a barrier to protect against the spread of infection between different users of the intraoral phototherapy device.

Figure 19A:
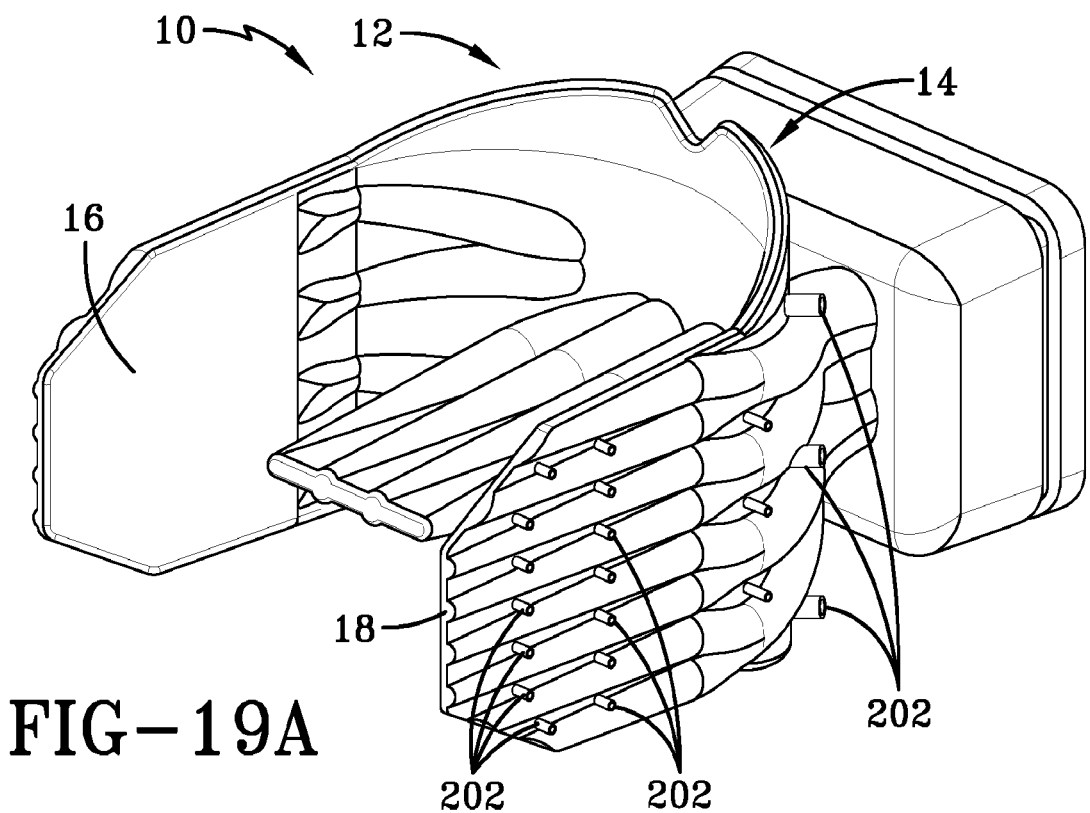
Figure 19B:
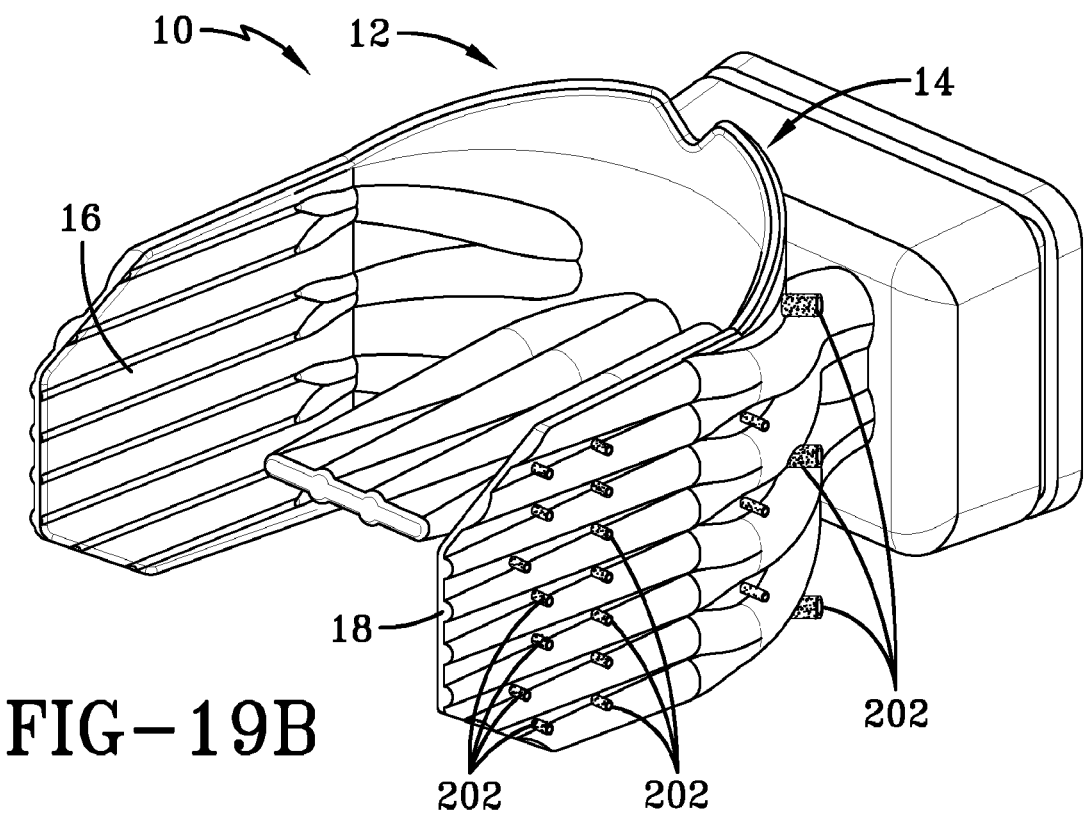
Figure 18C:
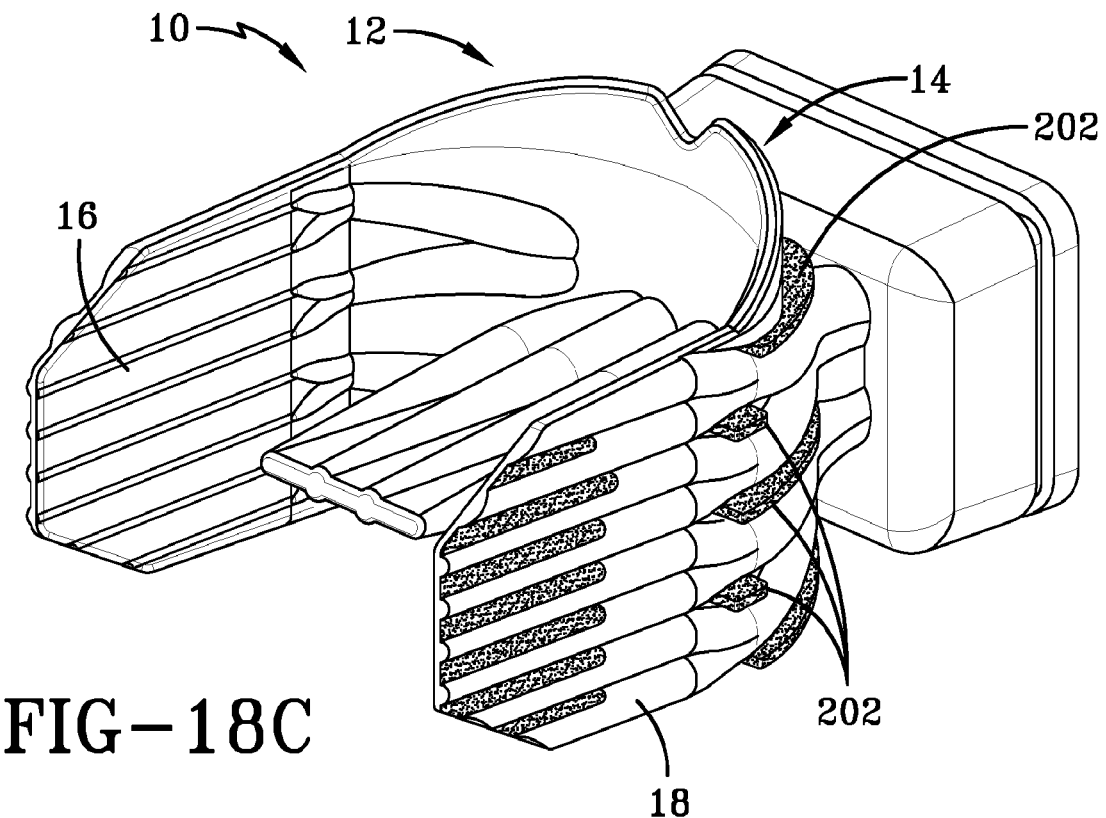
Figure 19C:
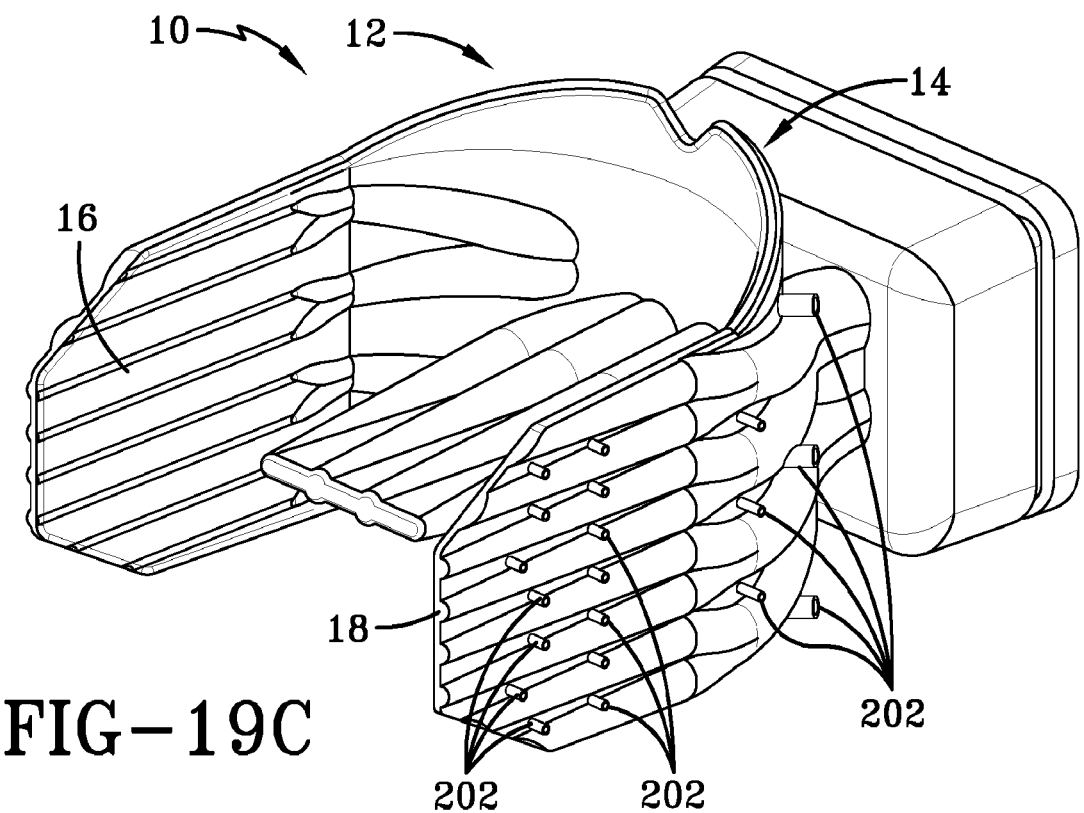

The interior surface of the sleeve or a surface of the intraoral phototherapy device at the point of contact between the sleeve and the intraoral phototherapy device (e.g., on the exterior of the intraoral phototherapy device) may be modified by adding separating features (e.g., roughening the surface as shown in FIG. 26) to further maintain the airgap between the sleeve and the intraoral phototherapy device. For example, FIGS. 18A-18C and FIGS. 19A-19C show the addition of separating features 202 located on an exterior surface of the intraoral phototherapy device. In FIGS. 18C and 19B, the separating features 202 are shown in a darker color to aid visualization of the features.

As will be understood by one of ordinary skill in the art, adding separating features may include adding or removing material from the sleeve or the intraoral phototherapy device. For example, the separating features may include (but are not limited to) standoffs, bosses, ridges, or hexagonal protrusions. As an example, the external surface of the intraoral phototherapy device may have a surface finish between 23 microns (SPI-B2) to 58 microns (SPI-C3) to maintain an airgap between the intraoral phototherapy device and the sleeve.

A spacing layer may be included between the sleeve and the intraoral phototherapy device. For example, the spacing layer may comprise a low-optical-interference fabric or a porous, soft, flexible mesh. The spacing layer may be located between the sleeve and the intraoral phototherapy device in order to trap air between the sleeve and the intraoral phototherapy device. The spacing layer may be attached to one or more of the intraoral phototherapy device or the sleeve. Alternatively, the spacing layer may not be attached to either of the intraoral phototherapy device or the sleeve.

As an alternative to or in addition to the sleeve, a hydrophobic foam coating may be used to maintain the airgap.

Figure 21C:
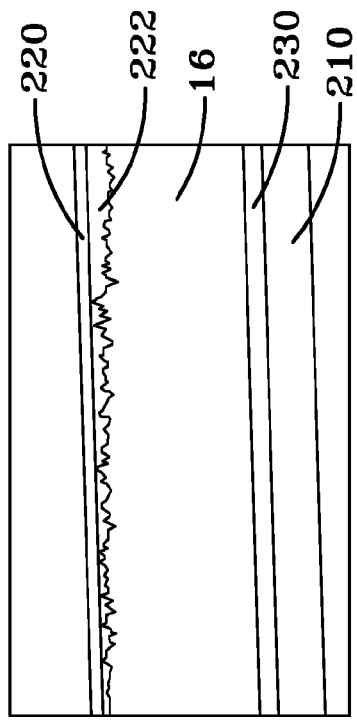
FIGS. 21B and 21C show a zoomed in portion of the phototherapy device of 21A.
Figure 21B:
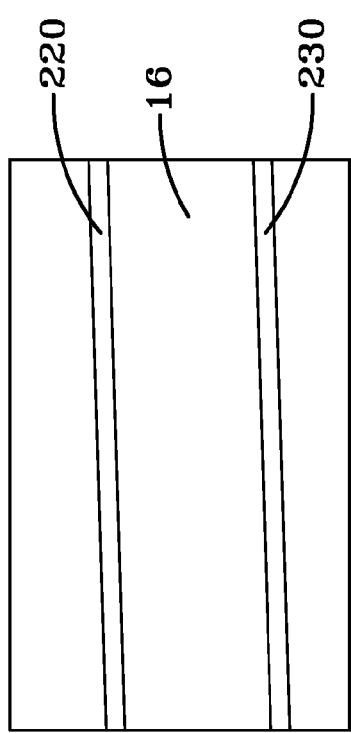
Figure 21A:
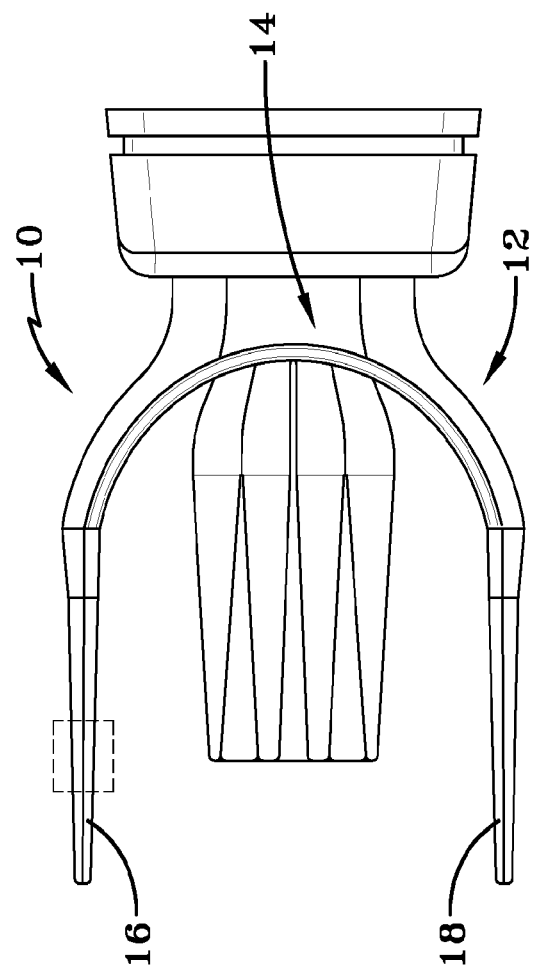
FIG. 21A shows a phototherapy device including a boxed region.
Figure 22:
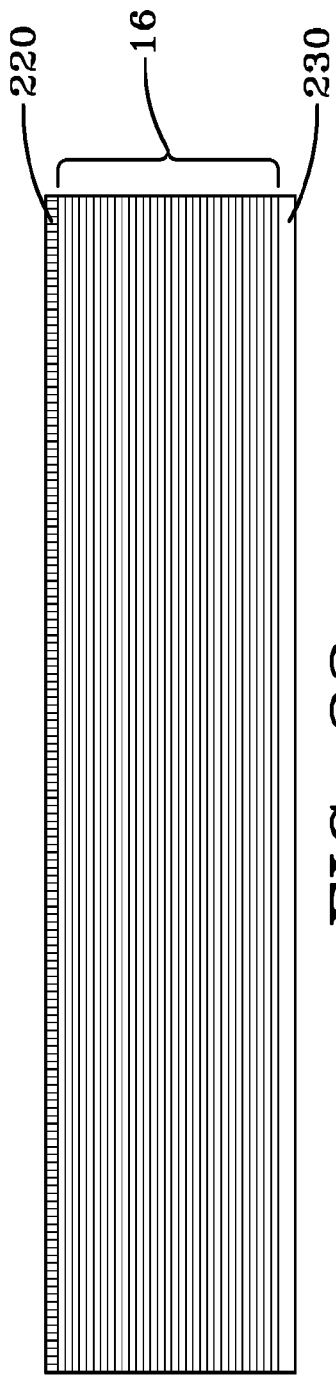
FIG. 22 shows a view of the layers of a phototherapy device including a cladding layer.
Figure 23:
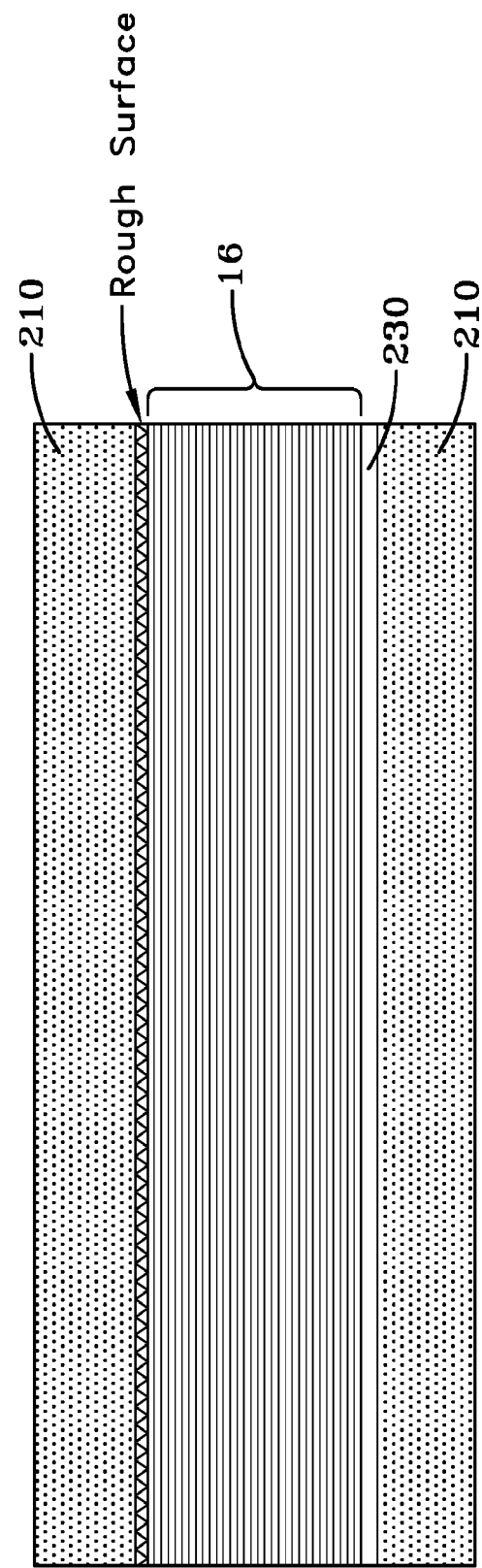
FIG. 23 shows a view of the layers of a phototherapy device including a roughed surface.

As shown in FIG. 21B, a cladding layer 220 may be applied to the surface of the intraoral phototherapy device in order to maintain TIR of light within the intraoral phototherapy device. FIG. 21A shows a zoomed in region (square) that is expanded in FIGS. 21B and 21C. FIGS. 21B and 22 show the layers of the side wing 16, cladding 220, and reflector 230. Also located outside the cladding 220 and reflector 230 are either air, tissue, or saliva. For comparison, FIG. 21C shows the layers of the sleeve 210, airgap 222, side wing 16, reflector 230, and sleeve 210. Also located outside the sleeve 210 may be air, tissue, or saliva (unlabeled). FIG. 22 also shows the layers of the sleeve 210 (labeled as disposable cover), roughened surface (i.e., separating features 202 shown in FIG. 26), intraoral phototherapy device (labeled as silicone mouthpiece), reflector 230.

The cladding layer may be configured to prevent/reduce contact between saliva/tissue and the intraoral phototherapy device. The cladding layer may have a refractive index that is less than or equal to 1.33 (e.g., lower than saliva and tissue). Alternatively, the cladding layer may have a refractive index between 1.33 and 1.5 and may be selectively added or removed in a controlled fashion. The cladding may be selectively added or removed to allow light to escape at locations where there is no cladding present.

The intraoral phototherapy device may include an identifier for differentiating between intraoral phototherapy devices. For example, the intraoral phototherapy device may include an RFID, serial number, barcode, 2D barcode, or any other suitable means for differentiating between different intraoral phototherapy device. For example, the identifier may be used to identify a particular intraoral phototherapy device associated with a particular patient.

Figure 24:
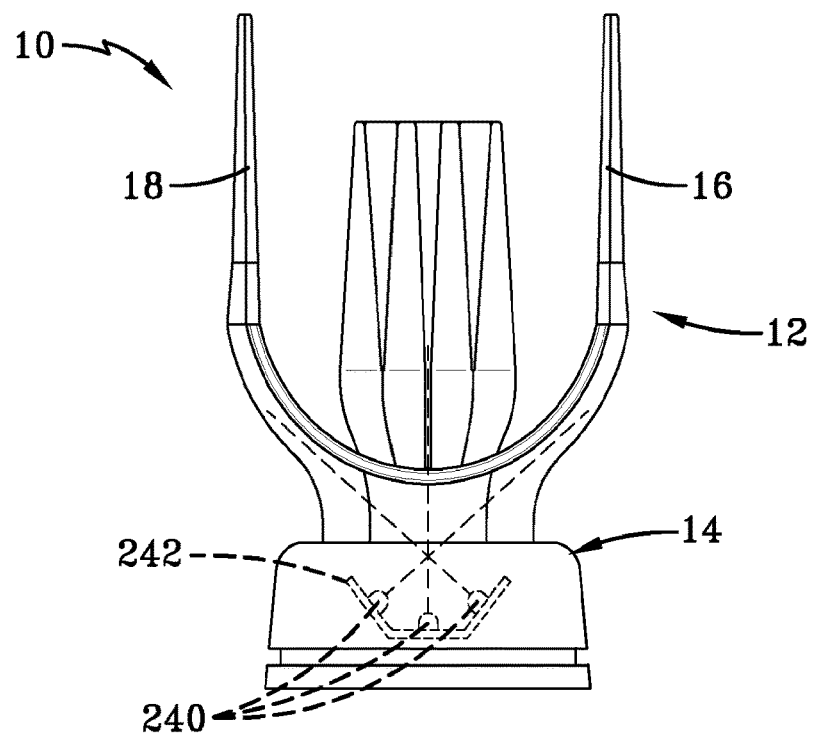
FIG. 24 shows a phototherapy device including light sources located within the phototherapy device.

Turning to FIG. 24, the a intraoral phototherapy device including light sources 240 within the main body portion 14 is shown. The light sources 240 may be attached to a printed circuit board 242. The printed circuit board 242 may be formed to control the direction of light travel within the intraoral phototherapy device. For example, as shown in FIG. 24, the printed circuit board 242 is formed so that light that has been emitted from the light source 240 enters the center flap 38 and the side wings 16, 18.

Figure 25:
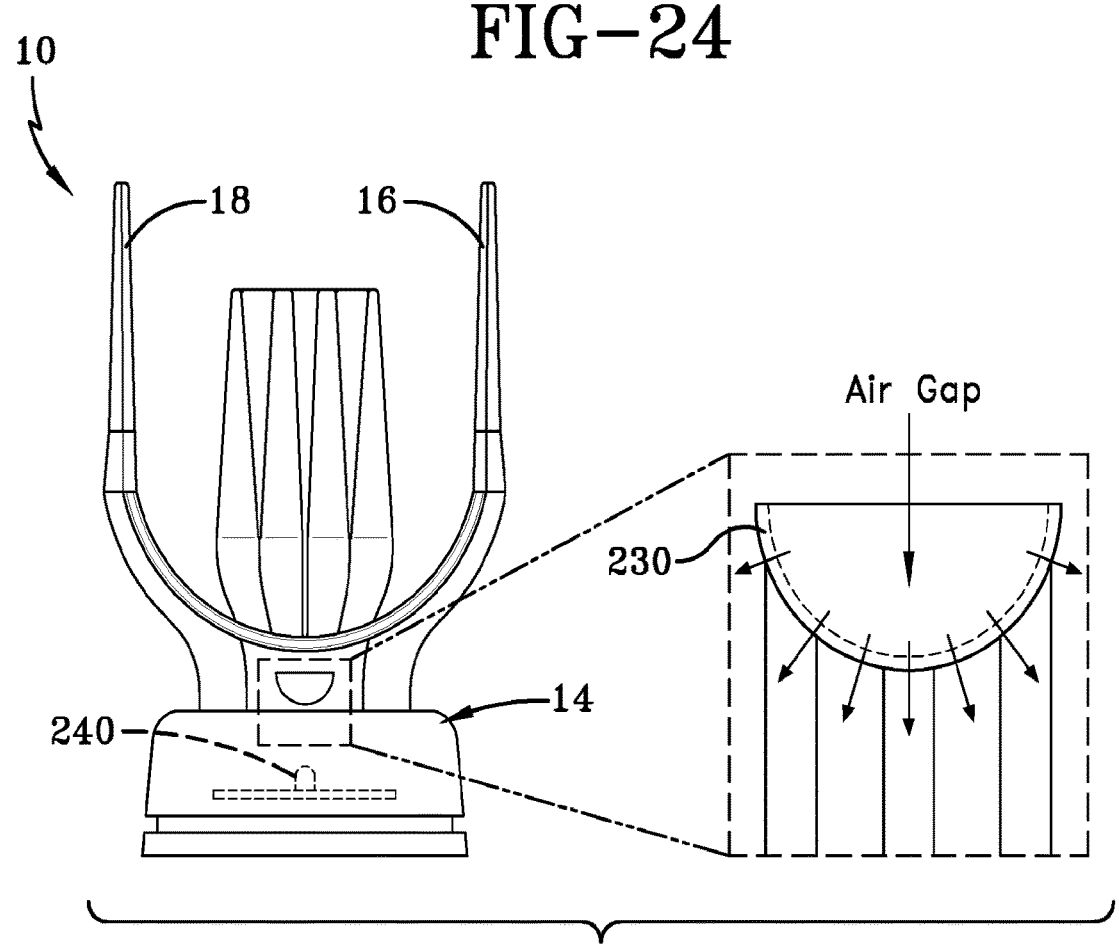
FIG. 25 shows a phototherapy device including an airgap and reflector.

Turning to FIG. 25, the intraoral phototherapy device ay include an airgap for redirecting light within the main body portion 14. A light source(s) 240 may be located such that light emitted by the light source 240 interacts with the airgap. The airgap 250 may reflect light towards an inner lip of a patient when the intraoral phototherapy device 10 is located in the patient's mouth. The airgap 250 reflects the light due to the index of refraction difference between the material of the intraoral phototherapy device and air. As shown in FIG. 25, the airgap 250 may also include a reflector 252.

Although the invention has been shown and described with respect to certain embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of a described component (e.g., that is functionally equivalent), even though not structurally equivalent to a disclosed component which performs the function of the herein illustrated exemplary embodiments of the invention. In addition, while a particular feature of the invention may have been disclosed with respect to a particular embodiment, such feature may be combined with one or more other features as may be desired or advantageous for any given or particular application.

ASPECT LIST

Any one or more of the below listed aspects may be combined.

Aspect 1. An intraoral phototherapy device for receiving light from an associated light source and propagating the light into an oral cavity of a patient, the device comprising:
an external light source; and
a light guide that receives light from the external light source, the light guide comprising a main body portion made of an optically transparent soft flexible biocompatible polymeric material sized and shaped to conform to contours of the oral cavity when inserted therein to direct the light to targeted regions of the oral cavity.

Aspect 2. The device of aspect 1 further comprising a controller for delivering the light to the light guide in a controlled manner.

Aspect 3. The device of any one of aspects 1-2 wherein the main body portion comprises a pair of laterally spaced side wings sized and shaped to be received between a patient's teeth and cheeks on opposite sides of the oral cavity for transmitting and directing the light to targeted regions of the oral cavity.

Aspect 4. The device of aspect 3 wherein the side wings support one or more solid side light channels integrally molded with the side wings for transmitting and directing the light to targeted regions of the oral cavity.

Aspect 5. The device of aspect 4 wherein at least some of the side light channels are generally cylindrical in shape and are selectively tapered along their length for controlled light emission therefrom.

Aspect 6. The device of any one of aspects 4-5 wherein at least some of the side light channels have at least two branches to more evenly distribute the light to the targeted portions of the oral cavity.

Aspect 7. The device of aspect 6 wherein at least some of the branches have at least two additional branches to more evenly distribute the light to the targeted regions of the oral cavity.

Aspect 8. The device of any one of aspects 6-7 wherein at least some of the branches are selectively tapered for controlled light emission therefrom.

Aspect 9. The device of any one of aspects 4-8 wherein at least some of the side light channels have disruptions or lenses along their length for controlled light emission.

Aspect 10. The device of any one of aspects 4-9 further comprising a reflective coating on inwardly facing sides of the side wings to reflect light outwardly through outwardly facing sides of the side light channels.

Aspect 11. The device of any one of aspects 4-10 wherein at least some of the side light channels utilize splitting to more evenly distribute the light to the targeted regions of the oral cavity.

Aspect 12. The device of any one of aspect 4-11 wherein rearwardly protruding ends of the side light channels protrude outwardly beyond the side wings, and the light source is optically coupled to the protruding ends of the side light channels.

Aspect 13. The device of aspect 12 wherein the light source comprises one or more LEDs that are embedded in the rearwardly protruding ends of the side light channels.

Aspect 14. The device of any one of aspects 1-13 wherein the light source is remotely coupled to the device via a fiber optic cable.

Aspect 15. The device of any one of aspects 1-14 wherein the light source comprises one or more LEDs.

Aspect 16. The device of any one of aspects 1-14 wherein the light source comprises a laser.

Aspect 17. The device of any one of aspects 3-16 wherein the side wings have a curvature that is contoured to mandibular and maxillary buccal surfaces of the oral cavity.

Aspect 18. The device of any one of aspects 3-17 wherein the main body portion further comprises a center flap intermediate the side wings for transmitting and directing the light to targeted regions of the oral cavity.

Aspect 19. The device of aspect 18 wherein the center flap includes one or more solid center light channels.

Aspect 20. The device of aspect 19 wherein the one or more center light channels have two or more branches to more evenly distribute the light to targeted regions of the oral cavity.

Aspect 21. The device of any one of aspects 18-20 wherein a forwardly facing end of the one or more center light channels projects light to a patient's tonsillar region.

Aspect 22. The device of any one of aspects 18-21 wherein the one or more center light channels are selectively tapered for controlled light emission therefrom.

Aspect 23. The device of any one of aspects 3-22 wherein one or more portions of the main body portion protrude rearwardly beyond the side wings.

Aspect 24. The device of aspect 23 wherein the light source is optically coupled to the protruding portions of the main body portion.

Aspect 25. The device of any one of aspects 23-24 wherein the light source comprises one or more LEDs that are embedded in the protruding portions of the main body portion.

Aspect 26. The device of any one of aspects 23-24 wherein the light source is remotely coupled to the protruding portions of the main body portion via a fiber optic cable.

Aspect 27. The device of any one of aspects 23-26 wherein the light source comprises one or more LEDs.

Aspect 28. The device of any one of aspects 23-26 wherein the light source comprises a laser.

Aspect 29. The device of any one of aspects 3-17 further comprising integral arcuate flexible top and bottom flaps that protrude upwardly and downwardly from arcuate joined rearward ends of the side wings for insertion between a patient's gums and lips to help stabilize the device against rotation during phototherapy treatment.

Aspect 30. The device of any one of aspects 3-17 further comprising bite pads on inwardly facing sides of the side wings intermediate the side wings' height adjacent innermost ends of the side wings for engagement by a patient's molar teeth to secure the side wings in place during phototherapy treatment.

Aspect 31. The device of aspect 18 wherein the center flap includes one or more solid center light channels.

Aspect 32. The device of aspect 31 wherein the center light channels have at least two branches to more evenly distribute the light to targeted regions of the oral cavity.

Aspect 33. The device of aspect 31 wherein one or more of the center light channels are selectively tapered for controlled light emission therefrom.

Aspect 34. The device of any one of aspects 31-33 wherein one side of the one or more center light channels has a flat reflective portion for reflecting light out the other side of the center light channels.

Aspect 35. The device of any one of aspects 31-34 wherein at least one of the one or more center light channels has disruptions or lens patterns to cause light to be emitted therefrom in a controlled manner.

Aspect 36. The device of any one of aspects 1-35 wherein the light source is contained in a housing attached to a rearwardly protruding end of the main body portion.

Aspect 37. The device of aspect 36 further comprising a cooling system for extracting heat away from the light source inside the housing.

Aspect 38. The device of aspect 37 wherein the cooling system is a liquid cooling system.

Aspect 39. The device of aspect 37 wherein the cooling system is a heat sink.

Aspect 40. The device of aspect 39 further comprising a fan for moving air past the heat sink.

Aspect 41. The device of any one of aspects 2-40 wherein the controller delivers constant light to the light guide.

Aspect 42. The device of any one of aspects 2-40 wherein the controller delivers pulsing light to the light guide.

Aspect 43. The device of any one of aspects 2-40 wherein the controller delivers multiple wavelengths of light to the light guide.

Aspect 44. The device of any one of aspects 2-40 wherein the controller includes sensors that monitor temperature in the oral cavity during phototherapy treatment.

Aspect 45. The device of any one of aspects 2-40 wherein the controller includes sensors that monitor one or more of pH, salinity, moisture, humidity, conductivity and resistivity in the oral cavity during phototherapy treatment.

Aspect 46. The device of any one of aspects 2-40 wherein the controller transmits monitored data from the oral cavity wirelessly during phototherapy treatment.

Aspect 47. The device of any one of aspects 2-40 wherein the controller monitors light output from the light source and changes input power to the light source to self-calibrate the light output from the light source.

Aspect 48. An intraoral phototherapy device for receiving light from an associated light source and propagating the light into an oral cavity of a patient, the device comprising:
an external light source,
a light guide that receives light from the light source, the light guide comprising a main body portion made of an optically transparent soft flexible biocompatible polymeric material sized and shaped to conform to contours of the oral cavity to direct the light via internal reflection to targeted portions of the oral cavity where light is emitted from the main body portion,
the main body portion comprising a pair of laterally spaced side wings sized and shaped for receipt between a patient's teeth and cheeks on opposite sides of the oral cavity for supporting one or more solid side light channels integrally molded with the side wings for transmitting and directing light to targeted regions of the oral cavity.

Aspect 49. The device of aspect 48 further comprising one or more solid center light channels intermediate the side wings for transmitting and directing light to targeted regions of the oral cavity.

Aspect 50. The device of aspect 49 wherein the side light channels and center light channels have at least two branches that more evenly distribute light to the targeted regions of the oral cavity.

Aspect 51. The device of any one of aspects 49-50 wherein the side light channels utilize splitting to more evenly distribute light to the targeted regions of the oral cavity.

Aspect 52. The device of any one of aspects 49-51 wherein rearward ends of the side light channels and center light channels protrude rearwardly beyond the side wings.

Aspect 53. The device of aspect 52 wherein the light source is optically coupled to the rearwardly protruding ends of the side light channels and center light channels.

Aspect 54. The device of aspect 53 wherein the light source comprises a plurality of LEDs embedded in the rearwardly protruding ends of the side light channels and center light channels.

Aspect 55. The device of aspect 52 wherein the light source is optically coupled to the rearwardly protruding ends of the side light channels and center light channels via a fiber optic cable.

Aspect 56. The device of any one of aspects 48-55 wherein the light source comprises one or more LEDs.

Aspect 57. The device of any one of aspects 48-55 wherein the light source comprises a laser.

Aspect 58. The device of any one of aspects 52-53 wherein the light source is contained in a housing attached to the rearwardly protruding ends of the side light channels and center light channels.

Aspect 59. The device of any one of aspects 48-58 further comprising bite pads on inwardly facing sides of the side wings intermediate the side wings' height adjacent innermost ends of the side wings for engagement by a patient's molar teeth to secure the side wings in place during phototherapy treatment.

Aspect 60. The device of any one of aspects 48-58 further comprising integral arcuate flexible top and bottom flaps that protrude upwardly and downwardly from arcuate joined rearward ends of the side wings for insertion between a patient's gums and lips to help stabilize the device against rotation during phototherapy treatment.

Aspect 61. The device of any one of aspects 48-60 further comprising a controller for delivering the light to the light guide in a controlled manner.

Aspect 62. The device of aspect 61 wherein the controller delivers constant light to the light guide.

Aspect 63. The device of aspect 61 wherein the controller delivers pulsating light to the light guide.

Aspect 64. The device of any one of aspects 61-63 wherein the controller delivers multiple wavelengths of light to the light guide.

Aspect 65. The device of any one of aspects 61-64 wherein the controller includes sensors that monitor temperature in the oral cavity during phototherapy treatment.

Aspect 66. The device of any one of aspects 61-65 wherein the controller includes sensors that monitor one or more of pH, salinity, moisture, humidity, conductivity and resistivity in the oral cavity during phototherapy treatment.

Aspect 67. The device of any one of aspects 61-66 wherein the controller transmits monitored data from the oral cavity wirelessly during phototherapy treatment.

Aspect 68. The device of any one of aspects 61-67 wherein the controller monitors light output from the light source and changes input power to the light source to self-calibrate the light output from the light source.

Aspect 69. A sleeve for maintaining an airgap around the intraoral phototherapy device of any of aspects 1-68, wherein the sleeve forms at least part of a boundary of an interior volume and the sleeve is of a shape to receive the main body portion of the intraoral phototherapy device within the interior volume.

Aspect 70. The sleeve of aspect 69 or the intraoral phototherapy device of any of aspects 1-68, further comprising a separating feature on an interior surface of the sleeve and/or on an external surface of the main body portion of the intraoral phototherapy device, wherein the separating feature is configured to maintain the airgap between the sleeve and the main body portion by blocking contact between the sleeve and the main body portion when the main body portion is located within the sleeve.

Aspect 71. The sleeve of aspect 70 or the intraoral phototherapy device of aspect 70, wherein the separating feature includes at least one of standoffs, bosses, ridges, or protrusions from the internal surface of the sleeve and/or the external surface of the main body portion.

Aspect 72. The sleeve of any of aspects 69-71 or the intraoral phototherapy device of any of aspects 70-71, further comprising:

a spacing layer located between the main body portion of the intraoral phototherapy device and the sleeve when the main body portion is located within the interior volume of the sleeve;

wherein the spacing layer comprises a porous material or a mesh.

Aspect 73. The intraoral phototherapy device of any of aspects 1-68 or 70-72, further comprising a cladding layer applied to an external surface of the main body portion.

Aspect 74. The intraoral phototherapy device of aspect 73, wherein the cladding layer has an index of refraction of less than or equal to 1.33 or between 1.33 and 1.5.

Aspect 75. The intraoral phototherapy device of any of aspects 73 or 74, wherein the cladding layer is applied to selective portions of the external surface of the main body portion.

What is claimed is:

1. An intraoral phototherapy device for directing light from an associated light source into an oral cavity of a patient, the device comprising:

a main body portion shaped to conform to contours of the oral cavity when inserted therein to direct the light to targeted regions of the oral cavity, wherein: the main body portion comprises a pair of laterally extending side wings free of biting projections:

has a u-shaped cross section along a central plane; and is sized and shaped to be received between a patient's teeth and cheeks on opposite sides of the oral cavity for transmitting and directing the light to the targeted regions of the oral cavity;

a central projection extending from the main body portion along a perpendicular line that is perpendicular to a line tangent to an apex of the main body portion, wherein the central projection extends along the central plane from an apex of the u-shaped cross section of the main body portion, past midway of the u-shaped cross section of the main body portion, and terminates at a distal edge of the central projection;

wherein the midway is located halfway between the line tangent to the apex and a line intersecting both distal ends of the u-shaped cross section of the main body portion;

wherein the main body portion is configured to emit the light from an outer surface; and wherein the central projection is configured to emit the light from the distal edge of the central projection.

2. The device of claim 1, wherein the main body portion has light emitting elements located along a length of its outer surface for controlled light emission, the light emitting elements including lenses or disruptions having a different index of refraction.

3. The device of claim 1, further comprising a reflective coating on an inner surface of the main body portion to reflect light outwardly through the outer surface of the main body portion.

4. The device of claim 1, further comprising integral arcuate flexible top and bottom flaps that protrude upwardly and downwardly from arcuate joined rearward ends of the main body portion for insertion between a patient's gums and lips to help stabilize the device against rotation during phototherapy treatment.

5. The device of claim 1, further comprising a sleeve for maintaining an airgap around the main body portion, wherein the sleeve forms at least part of a boundary of an interior volume and the sleeve is of a shape to receive the main body portion of the intraoral phototherapy device within the interior volume.

6. The device of claim 5, further comprising a separating structure on an interior surface of the sleeve and/or on an external surface of the main body portion, wherein the separating structure is configured to maintain the airgap between the sleeve and the main body portion by blocking contact between the sleeve and the main body portion when the main body portion is located within the sleeve.

7. The device of claim 1, further comprising a cladding layer applied to an external surface of the main body portion.

8. The device of claim 1, wherein the particular target regions of the oral cavity include at least one of (1) tonsillar tissues, (2) hard and soft palate tissues, (3) tongue tissues, or (4) a floor of a mouth of the patient.

9. The device of claim 1, wherein the particular target regions of the oral cavity include:
   (1) tonsillar tissues, (2) hard and soft palate tissues, and (3) tongue tissues; or
   (1) tongue tissues and (2) a floor of a mouth of the patient.

10. The device of claim 1, wherein the targeted regions of the oral cavity additionally include the lips.

11. The device of claim 1, further comprising a light source attached to the main body portion.

12. The device of claim 1, wherein the main body portion is made of an optically transparent material.

13. A phototherapy system including:
   the device of claim 1;
   a light source located external to the main body portion; and
   a light guide configured to receive light from the light source and transmit the received light to the main body portion.

* * * * *